(12) United States Patent
Reynolds

(10) Patent No.: US 12,409,121 B2
(45) Date of Patent: Sep. 9, 2025

(54) FORMULATIONS AND METHODS FOR PREPARING STABLE COSMETIC COMPOSITIONS

(71) Applicant: Spinart, LLC, Hazlet, NJ (US)

(72) Inventor: Garrett Reynolds, Colts Neck, NJ (US)

(73) Assignee: Spinart, LLC, Hazlet, NJ (US)

( * ) Notice: Subject to any disclaimer, the term of this patent is extended or adjusted under 35 U.S.C. 154(b) by 0 days.

(21) Appl. No.: 16/867,370

(22) Filed: May 5, 2020

(65) Prior Publication Data

US 2020/0352840 A1  Nov. 12, 2020

Related U.S. Application Data

(60) Provisional application No. 62/844,061, filed on May 6, 2019.

(51) Int. Cl.
| | |
|---|---|
| *A61K 8/44* | (2006.01) |
| *A61K 8/365* | (2006.01) |
| *A61K 8/368* | (2006.01) |
| *A61K 8/37* | (2006.01) |
| *A61Q 5/00* | (2006.01) |
| *A61Q 7/02* | (2006.01) |
| *A61Q 17/04* | (2006.01) |
| *A61Q 19/08* | (2006.01) |

(52) U.S. Cl.
CPC ............... *A61K 8/44* (2013.01); *A61K 8/365* (2013.01); *A61K 8/368* (2013.01); *A61K 8/375* (2013.01); *A61Q 5/006* (2013.01); *A61Q 7/02* (2013.01); *A61Q 17/04* (2013.01); *A61Q 19/08* (2013.01); *A61K 2800/30* (2013.01); *A61K 2800/524* (2013.01); *A61K 2800/58* (2013.01); *A61K 2800/59* (2013.01)

(58) Field of Classification Search
CPC ...................................................... A61K 8/44
See application file for complete search history.

(56) References Cited

U.S. PATENT DOCUMENTS

| | | | |
|---|---|---|---|
| 2,798,053 A | 7/1957 | Brown et al. | |
| 2,909,462 A | 10/1959 | Warfield et al. | |
| 3,755,560 A | 8/1973 | Dickert et al. | |
| 3,929,678 A | 12/1975 | Laughlin et al. | |
| 4,089,942 A | 5/1978 | Bore et al. | |
| 4,207,893 A | 6/1980 | Michaels | |
| 4,327,725 A | 5/1982 | Cortese et al. | |
| 4,421,769 A | 12/1983 | Dixon et al. | |
| 4,915,949 A | 4/1990 | Wong et al. | |
| 5,011,681 A | 4/1991 | Ciotti et al. | |
| 5,091,171 A | 2/1992 | Yu et al. | |
| 5,100,655 A | 3/1992 | Takano et al. | |
| 5,425,938 A | 6/1995 | Znaiden et al. | |
| 5,429,816 A | 7/1995 | Hofrichter et al. | |
| 5,487,884 A | 1/1996 | Bissett et al. | |
| 5,552,136 A | 9/1996 | Motley | |
| 5,643,588 A | 7/1997 | Roe et al. | |
| 5,667,789 A | 9/1997 | Collin et al. | |
| 5,690,967 A | 11/1997 | Yu et al. | |
| 5,886,041 A | 3/1999 | Yu et al. | |
| 6,267,978 B1 | 7/2001 | Sang et al. | |
| 6,413,310 B1 * | 7/2002 | Tamatsuka | ............... C30B 29/06 |
| | | | 257/E21.321 |
| 6,419,954 B1 | 7/2002 | Chu et al. | |
| 6,596,264 B2 | 7/2003 | Terren et al. | |
| 6,946,120 B2 | 9/2005 | Wai-Chiu So et al. | |
| 7,416,722 B2 | 8/2008 | Straetmans et al. | |
| 7,449,613 B2 | 11/2008 | Klofta et al. | |
| 8,017,128 B2 | 9/2011 | Mekideche | |
| 9,789,070 B2 * | 10/2017 | Carullo | ................... A61K 36/28 |
| 2002/0028226 A1 | 3/2002 | Terren et al. | |
| 2007/0269379 A1 | 11/2007 | Mitragotri et al. | |
| 2016/0128328 A1 | 5/2016 | Sawyer et al. | |
| 2019/0169117 A1 * | 6/2019 | Weinberger | ........... C07C 279/14 |

FOREIGN PATENT DOCUMENTS

| | | | | |
|---|---|---|---|---|
| CN | 108478498 | A * | 9/2018 | |
| EP | 0673648 | A1 | 9/1995 | |
| EP | 616799 | B1 * | 5/2000 | ............... A61K 8/14 |
| EP | 1709955 | A1 | 10/2006 | |
| FR | 6838 | M * | 3/1969 | |
| FR | 2756489 | A1 | 6/1998 | |
| WO | 2000/069403 | A1 | 11/2000 | |
| WO | 2012/177433 | A1 | 12/2012 | |
| WO | WO-2018101443 | A1 * | 6/2018 | ......... A61K 31/4709 |

OTHER PUBLICATIONS

Anand, S.P. and Sati, N. (2013) "Artificial Preservatives and their Harmful Effects: Looking Toward Nature for Safer Alternatives." International Journal of Pharmaceutical Sciences and Research, 4(7): 2496-2501.
Bhalla, T.C., et al., Advances in Industrial Biotechnology Ram Sarup Singh, Ashok Pandey & Christian Larroche (Eds.) IK International Publishing House Pvt. Ltd., India pp. 56-76 (2014).
Cosmetic Bench Reference, pp. 1.19-1.22 (1996).
Dermal Exposure Assessment: Principles and Applications, EPA/600/8-91/011b, Jan. 1992, Interim Report—Exposure Assessment Group, Office of Health and Environmental Assessment, U.S. Environmental Protection Agency, Washington, D.C. 20460.
Fitch, C.A., et al., "Arginine: Its pKa value revisted." Protein Science 2015, (24): 752-761.

(Continued)

*Primary Examiner* — Gina C Justice

(74) *Attorney, Agent, or Firm* — Bochner PLLC; Beverly W. Lubit

(57) ABSTRACT

The described invention provides cosmetic formulation stabilizing systems comprising an arginine component and organic acid component, for preserving cosmetic formulations, stable cosmetic and dermatologic formulations comprising the cosmetic formulation stabilizing system, methods for manufacturing the same, and the use of such compositions for skin care.

8 Claims, No Drawings

(56) References Cited

OTHER PUBLICATIONS

The Merck Index—An Encyclopedia of Chemicals, Drugs, and Biologicals. Budavari, S. (ed.). Merck and Co., Inc., Whitehouse Station, NJ: 1996, p. 817.

Thiemann, A., et al (2014) "The Formulator's Guide to Safe Cosmetic Preservation" Personal Care 5: 39-43.

Sciarra, J.J. et al., Chapter 50: Aerosols, in Remington: The Science and Practice of Pharmacy, 20th Edition, Eds. Paul Beringer et al., 2000, pp. 963-979, Lippincott, Williams & Wilkins, Philadelphia, PA.

Sethi et al., Moisturizers: The Slippery Road, Ind. J. Dermatol. 61:279-87 (2016).

Kang et al., Moisterizer in Patients with Inflammatory Skin Diseases, Medicina 58:888 (2022).

Chularojanamontri et al., Moisterizers for Acne What are their Constituents?, J. Clin. Aesthet. Dermatol. 7:36-44 (2014).

European Search Report, EP Appl. No. 20802197.2 dated Apr. 17, 2023 (12 pgs.).

Kasten G., et al, "In vitro and in vivo comparison between crystalline and co-amorphous salts of naproxen arginine", European Journal of Pharmaceutics and Biopharmaceutics, vol. 132, Nov. 1, 2018 (Nov. 1, 2018 ), pp. 192-199.

Examination Report of the Australian Patent Office in related AU Patent Appl. No. 2020267406, dated Dec. 16, 2024, 4 pages.

Kasten, G. et al., "In vitro and in vivo comparison between crystalline and co-amorphous salts of naproxen-arginine", European Journal of Pharmaceutics and Biopharmaceutics, vol. 132, pp. 192-199, Nov. 2018.

Office Action of the Korean Intellectual Property Office in related Korean Appl. No. 10-2021-7039829, dated Nov. 27, 2024, 5 pages.

\* cited by examiner

FORMULATIONS AND METHODS FOR PREPARING STABLE COSMETIC COMPOSITIONS

CROSS-REFERENCE TO RELATED APPLICATIONS

This application claims the benefit of priority to provisional application 62/844,061 (filed May 6, 2019), the contents of which are incorporated by reference in their entirety.

FIELD OF INVENTION

The described invention relates to cosmetic composition stabilization systems, and formulations and methods for preparing stable cosmetic and dermatologic compositions containing the systems.

BACKGROUND

The complex development process for cosmetics involves multiple stages and many different disciplines. Disciplines include the biology, chemistry and mechanics of the skin as well as biology, chemistry, and mechanics of the formulation. Indeed, many factors must be evaluated and considered to insure that the final product is safe, effective, and aesthetically pleasing to the end user, as well as being cost-effective, safe and efficient to manufacture. There are a number of considerations that must be weighed to bring a final formulation to a full marketable product (Farris, Patricia K. Cosmeceuticals and Cosmetic Practice. John Wiley & Sons Ltd, 2014).

Industry Considerations

The ability to use a broad range of materials in cosmetic and dermatologic (meaning of the skin, hair and nails) formulations in a cost efficient and effective manner is important to the cosmetic industry. There are a broad range of raw materials that can be utilized in formulations, which presents a challenge for researchers or chemists in the field. They must select ingredients that can be handled and introduced into industry scale production without causing issues with safety and complicated processing, which can result in challenges with costs and quality.

Raw materials in powder form require specific equipment that must be selected and engineered to allow the powders to be safely, effectively and cost-efficiently solubilized into cosmetic and dermatological formulations. Also, in addition to the handling requirements, but also equally important, is the consideration of the specific conditions require to bring challenging raw materials into formulation. Due to the nature of many raw materials, there are specific conditions that need to be met, such as, temperature, mixing time, mixing energy, order of addition, presence of solubilizing agents, pH, and vessel design to name a few.

Formulation Considerations

The skin, while extremely effective in protecting the body against outside harmful substances and preserving inner biological activity, requires cosmetic care to maintain it in good condition. Cosmetic formulations are applied topically and are generally known as topical agents.

Cosmetics and topical agents frequently include particular compounds which may require extensive processing on the front end and thermodynamic, chemical, and environmental stability considerations. For example, cosmetic formulations can include lipids, which are known to be unstable and are vulnerable to crystallization, degradation, and contamination.

Crystallization or sedimentation of cosmetic formulations can result from a number of external factors, such as temperature fluctuation or the presence of pressure, as well as internal factors, such as chemical or enzymatic interesterification, fractionation, blending, and the use of certain formulation manipulation methods such as encapsulating lipids into small droplets as an oil/water emulsion. The control of the crystallization process is commonly challenged by technical complexity and practical constraints on the production process. (Sato Kiyotaka. Crystallization of Lipids: Fundamentals and Applications in Food, Cosmetics, and Pharmaceuticals. Wiley Blackwell, 2018).

Microbes, such as bacteria, fungi and yeast, can enter cosmetic products through insufficient or unregulated handling and temperature control procedures at any stage of product development including, without limitation, in the raw materials, and during the manufacturing, packaging, shipment and storage of the product. Microbial contamination with pathogenic microorganisms can pose a health risk, for example, the growth of *Pseudomonas* bacteria may cause an infection in the eyes and can lead to vision loss.

Historically, cosmetic manufacturers utilize preservatives in order to prevent contamination by microbial growth. Preservatives can be used to further ensure the integrity of topical agents and prolong shelf life stability by preventing breakdown of organic compounds in cosmetic ingredients, such as oil.

Preservatives used in topical agents can generally be organized into two groups: formaldehyde donors and substances that do not produce formaldehyde. Formaldehyde donors include: DMDM hydantoin, diazolidinyl urea, imidazolindinyl urea, and quaternium 15. Non-formaldehyde producing substances include substances such as: isothiazolinones, phenoxyethanol, chlorinated aromatic compounds, and para-hydroxybenzoic acids (parabens), and iodopropunyl butylcarbamate. (Barel, A. O., et al. Handbook of Cosmetic Science and Technology. Taylor & Francis, 2014). Specifically, preservatives commonly found in topical agents include: KATHON® CG methyl(chloro)isothiazolinonformaldehyde, methyldibromo glutaronitrile mixed with phenoxyethanol (Euxyl K400) parabens, benzalkonium chloride, cetrimide, ethylenediaminetetraacetic acid (EDTA), benzoic acid, thiomersal, imidurea, chlorhexidine, chlorocresol, and phenyl salicylate.

While various substances can be added to the cosmetic formulations to prevent instability, it may not necessarily be desirable to utilize certain substances. The skin is the largest organ of the body, and because topical agents are applied to skin, cosmetic ingredients are therefore directly administered to the body and may be absorbed into the blood stream. For example, concerns have recently arisen that preservatives are linked to detrimental or even life threatening side effects, such as hypersensitivity, asthma, and cancer. (Anand and Sati (2013) "Artificial Preservatives and their Harmful Effects: Looking Toward Nature for Safer Alternatives." International Journal of Pharmaceutical Sciences and Research, 4(7): 2496-2501).

There are limited methods to avoid or limit the use of synthetic chemicals in a cosmetic formulation. For example, if a topical agent contains high concentrations of ethyl alcohol, then preservatives are generally believed not necessary to prevent contamination and ensure product integrity. Similarly, branched-chain higher alcohols may inhibit crystallization. However, alcohols will degrade organic compounds, and alcohol, which is further considered a drying agent, is used in limited quantities in cosmetic formulations. In another example, machinery such as microfluidizers or high-pressure homogenizers may be used to produce large mechanical forces (shearing, impact, and vacitation) during the production process that may rupture microbial contaminants and break up crystallization. (Elsner, Peter, et al. Cosmeceuticals and Active Cosmetics. CRC Press/Taylor & Francis, 2016). However, the impact of such high pressure forces on the remainder of the cosmetic ingredients may render this method undesirable for use in production and manufacture. Furthermore, the pH value of the cosmetic product may be altered to be a biocide and prevent microbial growth.

Another issue with cosmetics formulation preparation is the effectiveness of the cosmetic upon delivery. Cosmetic effectiveness is dependent on bioavailability of the cosmetic and the delivery, penetration, and absorption of the cosmetic at the targeted sites of delivery. Therefore, the use of stabilizers that disrupt the bioavailability and/or the penetration of the active agent (meaning the ingredient, component or constituent of the composition responsible for the intended cosmetic effect) will render the cosmetic ineffective and therefore less desirable for the consumer.

Formulators must also consider consumer interaction with cosmetic formulations once purchased. For products such as face creams and other topical agents that are stored in jars, the consumer will typically dip his/her finger into the jar in order to extract the desired amount of topical agent. Additionally, topical agents tend to be used over a period of weeks to months. In this context, once topical agents are in the care of consumers, they must be able to withstand exposure to microbes, oxidation, sunlight, temperature changes, and the test of time.

Organic Acid Stabilization

The use of organic acids and their salts has been characterized as being able to stabilize cosmetics long enough to prolong shelf life, prevent crystallization, and prevent growth of bacteria, yeast, and fungi. For example, organic acids are useful in cosmetic formulations to kill bacteria because they are able to penetrate into a microorganism through the cell wall and cell membrane, where they lower the pH value of the cell which ultimately leads to the death of the microorganism. (Theimann and Jänichen-Dr. Straetemans, Germany (2014) "The Formulator's Guide to Safe Cosmetic Preservation" Personal Care 5: 39-43).

The challenge of utilizing organic acids in cosmetic formulations is their limited solubility in aqueous systems. Without solubilization and neutralization of organic acids, their limited solubility makes it impractical to introduce them into cosmetic formulations in a stable and reliable manner.

In a solution, the molecules of the solute (or dissolved substance) are uniformly distributed among those of the solvent. The solubility of a compound in a particular solvent is an inherent characteristic of the compound. The relative affinities of the solute molecules and the solid phases determine solubility. The solubility of a compound is a specific thermodynamic property, and an imbalance in a thermodynamic state will cause a change toward re-establishing a balance within the system. Because solubility is a specific thermodynamic property, any imbalance that causes a change away from solubility equilibrium will result in a change in the system toward re-establishing balance.

The physicochemical properties of a compound may be manipulated by changing the surrounding environment. For example, the solubility of an ionizable compound can be greatly increased by changing the pH of the solution to a value at which the compound is in its ionized form. However, attempts to advantageously manipulate one particular physicochemical property can negatively impact another property. For instance, in designing a liquid formulation, a formulator may attempt to increase a compound's solubility by manipulating pH, but the altered pH may negatively impact other aspects of the formulation, such as interfering with the stability of the formulation (meaning the capability of a particular formulation to remain within its physical, chemical, microbiological, therapeutic and toxicological specifications).

For example, formulators may turn to various neutralizing agents to neutralize the organic acids and adjust the pH levels. Alkalis such as NaOH, KOH, TEA, and AMP are commonly used in cosmetic formulations. However, generally large amounts of a neutralizer are needed to achieve organic acid stability, and the neutralizing agent may not completely solve the issue at hand. The saturation point of the alkali acid complex is fairly low, which limits the amount of acid that can be neutralized. Typically, additional stabilizers, such as co-solvents or buffering agents, must be also used.

For example, some formulators have also had to add humectants with water-attracting properties to further stabilize organic acids in solution. Exemplary humectant ingredients include, without limitation, glycerol or glycols, e.g. propylene glycol, butylene glycol, dipropylene glycol, or 2-methylpropanediol, which belong to the group of polyols; esters of polyglycerol, e.g. polyglyceryl-10 laurate, or esters of sorbitan, e.g. sorbitan laurate. However, while glycerin hinders recrystallization, it does not allow for acid solubility to increase.

Humectants have been used as cosmetic compounds for as long as cosmetics have existed. They include natural materials such as honey, aloe, or glycerin, and are typically mild. The property that makes humectants useful is their ability to attract and hold water like a sponge. In fact, glycerin can hold as much as three times its weight in water. However, the use of glycerin as a humectant and an organic acid as a preservative/neutralizing agent in compositions at pH 7.0 to 8.0 is generally insufficient, because cosmetic or dermatologic formulations lacking a preservative may need to be acidic for the organic acid to function as a antimicrobial agent. Attempts at lowering the pH by including more organic acids may result in product instability and may require further adjustments of pH and humectants in order to stabilize. The use of these substances may therefore require further evaluation on their effect on the delivery and effectiveness of the active ingredient.

The complexities of topical agent formulation are further complicated by the manufacturing process, storage, and delivery and interaction with the skin and the desires of the consumer as discussed supra. While the use of neutralizers, and related required additional stabilizers, with organic acids may solve many of the above issues, consumers have expressed a preference for cosmetic formulations that have fewer ingredients, more natural ingredients, and have more effective active agents. As such, there is a need in the art for multifunctional ingredients that address these needs.

Arginine

Arginine is a basic amino acid that occurs naturally and also may be synthesized. It has one carboxylic group, one amino group, and one guanido group at the end of a 3-carbon aliphatic side chain. The main properties of arginine are provided in Table 1. (Libretexts. "23.3: The Acid-Base Properties of Amino Acids." Chemistry LibreTexts, University of California Davis); (Budavari, S. (ed.). The Merck Index—An Encyclopedia of Chemicals, Drugs, and Biologicals. Whitehouse Station, N.J.: Merck and Co., Inc., 1996, p. 817).

TABLE 1

Properties of Arginine

| Property | Value |
|---|---|
| α-CO$_2$H pKa1 | 2.18 |
| α-NH$_3$ pKa2 | 9.09 |
| Side Chain pKa3 | 12.5-13.8 |
| pI | 10.8 |

As can be seen from the pKa1 of the carboxylic group, the carboxyl moiety is strongly acidic. In contrast, the guanido group's pKa3 reflects the exceptionally high basicity of this moiety at the end of the guanido side chain. This group is able to form multiple hydrogen bonds ("H-bonds"). The basic function in arginine is attributable to the onium cations (meaning mononuclear cations derived by addition of a hydron to a mononuclear parent hydride, e.g., $NH_3^+$)) at pH less than 8, which are unreactive when they exist as the onium conjugate acid (a conjugate acid contains one more H atom and one more+charge than the base that formed it). Thus, because the guanidinium group is positively charged in neutral, acidic, and even most basic environments, solute molecules of arginine carry an excess positive charge. (Id). The planar guanidium group often partakes in ionic (meaning the complete transfer of valence electron(s) between atoms) interactions and hydrogen bonding (meaning an attractive force occurring in polar compounds in which an H atom of one molecule is attracted to two unshared electrons of another) interactions critical to maintaining stability in organic complexes. (Fitch et al., "Arginine: Its pKa value revisted." Protein Science 2015, (24): 752-761). Physiologically, arginine has the unusual ability to remain ionized under all physiological conditions including physiological pH. In addition, arginine may be multifunctional and/or synergistic in its interaction with other ingredients.

The described invention provides a solution to the formulation challenges listed above and provides stable, effective, and aesthetically pleasing compositions for the consumer.

SUMMARY OF THE INVENTION

According to one aspect, the described invention provides a cosmetic composition stabilization system comprising an arginine-component comprising: i) an arginine compound, and an organic acid compound, and a solvent; wherein the arginine compound is an arginine, a conjugate, or an analog thereof represented by Formula VI,

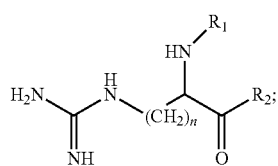

Formula VI wherein $R_1$ represents a hydrogen atom, a hydroxyl group, an acyl or acyloxy radical, or an amino acid substituted or not on its free α-amino function, bound by a peptide bond; $R_2$ represents a hydroxyl group, an amine, alkylamine or alcoxy radical, a silyloxy group, or an amino acid substituted or not on its free α-carboxylic function, bound by a peptide bond; and n represent 3 or 4; the organic acid compound is an organic acid, a conjugate, or a derivative thereof; wherein the arginine compound and the organic acid compound form a complex and the complex is effective as a preservative of a cosmetic or dermatologic composition, to solubilize the organic acid and to stabilize the finished product/cosmetic or dermatologic composition at pH 4.5-5.5 without including a humectant.

According to some embodiments, the solvent is water. According to some embodiments, the organic acid is a carboxylic acid. According to some embodiments, the carboxylic acid is a hydroxy acid. According to some embodiments, the hydroxy acid is an alpha hydroxy acid. According to some embodiments, the organic acid compound is two organic acids selected from anisic acid, levulinic acid, mandelic acid, salicylic acid, sorbic acid, benzoic acid, ferulic acid and syringic acid. According to another aspect, the described invention provides a method of preparing the cosmetic or dermatologic composition comprising (a) preparing the organic acid of the cosmetic composition stabilizing system as a greater than 20% solution (w/w %) to form the organic acid compound; (b) combining the arginine compound and the organic acid compound to form the cosmetic composition stabilizing system; and (c) combining the cosmetic composition stabilizing system and a cosmetically acceptable carrier to form the cosmetic or dermatologic composition; and adjusting pH of the finished product/ cosmetic or dermatologic composition as needed to pH 4.5-5.5. According to another embodiment, the method of preparing the cosmetic or dermatologic composition further comprises formulating the cosmetic or dermatologic composition with an active agent. According to another embodiment, a method of treating a skin condition of a subject in need thereof comprises preparing the cosmetic or dermatologic composition comprising the active agent, and administering the prepared cosmetic or dermatologic composition comprising the active agent topically to the subject, wherein the active agent comprises one or more of an anti-acne agent, a skin lightening-agent, a hair growth agent, a hair retardation agent, an anti-dandruff agent, an anti-irritation agent, an anti-oxidants/radical scavenger agent, an anti-inflammatory agent, a wound-healing agent, an anti-viral agent, an anti-wrinkle agent, a moisturizing agent, an anti-fungal agent, an anti-bacterial agent, an enzyme, a ceramide, a sunscreen, a plant extract, a vitamin, or urea.

According to another aspect of the described invention, a cosmetic composition stabilization system comprises an arginine-component, and a glyceryl monoester wetting agent, wherein the arginine component comprises an arginine compound, and an organic acid compound, and a solvent; wherein the arginine compound is an arginine, a conjugate, or an analog thereof represented by Formula VI,

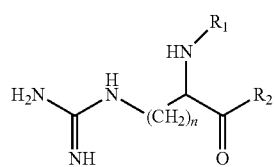

Formula VI wherein: $R_1$ represents a hydrogen atom, a hydroxyl group, an acyl or acyloxy radical, or an amino acid substituted or not on its free α-amino function, bound by a peptide bond; $R_2$ represents a hydroxyl group, an amine, alkylamine or alcoxy radical, a silyloxy group, or an amino acid substituted or not on its free α-carboxylic function, bound by a peptide bond; and n represent 3 or 4; the organic acid compound is an organic acid, a conjugate, or a derivative thereof; wherein the arginine compound and the organic acid compound form a complex; the complex is effective as a preservative of the composition, to solubilize the organic acid and to stabilize the finished product/the cosmetic or dermatologic composition at pH 6-6.5 without including a humectant; and the solution remains clear and stable over multiple freeze thaw cycles.

According to some embodiments, the glyceryl monoester wetting agent is glyceryl caprylate/caprate. According to some embodiments, the solvent is water. According to some embodiments, the organic acid is a carboxylic acid. According to some embodiments, the carboxylic acid is a hydroxy acid. According to some embodiments, the hydroxy acid is an alpha hydroxy acid. According to some embodiments, the organic acid compound is two organic acids selected from anisic acid, levulinic acid, mandelic acid, salicylic acid, sorbic acid, benzoic acid, ferulic acid and syringic acid.

According to some embodiments, a method of preparing a cosmetic or dermatologic composition comprises (a) preparing the organic acids of the cosmetic composition stabilizing system as a greater than 20% solution (w/w %) to form the organic acid compound; (b) combining the arginine compound, the organic acid compound, and the wetting agent to form the cosmetic composition stabilizing system; (c) combining the cosmetic composition stabilizing system and a cosmetically acceptable or pharmaceutically acceptable carrier to form the cosmetic or determatologic composition, and (d) adjusting pH of the cosmetic or dermatologic composition to pH 6-6.5 as needed.

According to some embodiments, the method of preparing the cosmetic or dermatologic composition further comprises formulating the cosmetic or dermatologic composition with an active agent. According to some embodiments, a method for treating a skin condition of a subject in need thereof comprises formulating the cosmetic or dermatologic compositions with an active agent, and administering the cosmetic or dermatologic composition topically to the subject, wherein the active agent comprises one or more of an anti-acne agent, a skin lightening-agent, a hair growth agent, a hair retardation agent, an anti-dandruff agent, an anti-irritation agent, an anti-oxidants/radical scavenger agent, an anti-inflammatory agent, a wound-healing agent, an anti-viral agent, an anti-wrinkle agent, a moisturizing agent, an anti-fungal agent, an anti-bacterial agent, an enzyme, a ceramide, a sunscreen, a plant extract, a vitamin, or urea.

DETAILED DESCRIPTION OF EMBODIMENTS

Definitions

As used herein and in the appended claims, the singular forms "a", "an", and "the" include plural reference unless the context clearly dictates otherwise. Thus, for example, reference to a "peptide" is a reference to one or more peptides and equivalents thereof known to those skilled in the art, and so forth.

As used herein, the term "about" means plus or minus 20% of the numerical value of the number with which it is being used. Therefore, about 50% means in the range of 40%-60%.

The term "active agent" as used herein refers to the ingredient, component or constituent of a composition responsible for the intended cosmetic effect. The terms "skin care ingredient" and "active agent" are used interchangeably.

The term "administer" as used herein means to give or to apply. The term "administering" as used herein includes in vivo administration, as well as administration directly to tissue ex vivo.

The terms "animal," "patient," and "subject" as used herein include, but are not limited to, humans and non-human vertebrates such as wild, domestic and farm animals. According to some embodiments, the terms "animal," "patient," and "subject" may refer to humans. According to some embodiments, the terms "animal," "patient," and "subject" may refer to non-human mammals.

The term "analog" as used herein refers to a compound whose structure is related to that of another compound but whose chemical and biological properties may be quite different. A "direct analog" possesses chemical and pharmacological similarities to an existing compound; a "structural analog" possesses structural similarities only; it can differ in one or more atoms, functional groups or substructures and have different physical, chemical, biochemical or pharmacological properties. The term "functional analog" as used herein refers to chemically different compounds displaying similar pharmacological properties.

The term "anti-inflammatory agent" as used herein refers to a therapeutic agent that counteracts and inhibits the process of inflammation and swelling. The term "non-steroidal anti-inflammatory agent" as used herein refers to a large group of agents that are aspirin-like in their action, including, but not limited to, ibuprofen (Advil®), naproxen sodium (Aleve®), and acetaminophen (Tylenol®). Additional examples of non-steroidal anti-inflammatory agents that are usable in the context of the described invention include, without limitation, oxicams, such as piroxicam, isoxicam, tenoxicam, sudoxicam, and CP-14,304; disalcid, benorylate, trilisate, safapryn, solprin, diflunisal, and fendosal; acetic acid derivatives, such as diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac; fenamates, such as mefenamic, meclofenamic, flufenamic, niflumic, and tolfenamic acids; propionic acid derivatives, such as benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic; pyrazoles, such as phenylbutazone, oxyphenbutazone, feprazone, azapropazone, and trimethazone. Mixtures of these non-steroidal anti-inflammatory agents also may be employed, as well as the dermatologically acceptable salts and esters of these agents. One example is etofenamate, a flufenamic acid derivative.

The term "anti-oxidant agent" as used herein refers to a substance that inhibits oxidation or reactions promoted by oxygen or peroxides. Non-limiting examples of anti-oxidants include ascorbic acid (vitamin C) and its salts, ascorbyl esters of fatty acids, ascorbic acid derivatives (e.g., magnesium ascorbyl phosphate, sodium ascorbyl phosphate, ascorbyl sorbate), tocopherol (vitamin E), tocopherol sorbate, tocopherol acetate, other esters of tocopherol, butylated hydroxy benzoic acids and their salts, 6-hydroxy-2,5, 7,8-tetramethylchroman-2-carboxylic acid (commercially available under the tradename Trolox®, gallic acid and its alkyl esters, especially propyl gallate, uric acid and its salts and alkyl esters, sorbic acid and its salts, lipoic acid, amines (e.g., N,N-diethylhydroxylamine, amino-guanidine), sulfhydryl compounds (e.g., glutathione), dihydroxy fumaric acid and its salts, glycine pidolate, arginine pilolate, nordihydroguaiaretic acid, bioflavonoids, curcumin, lysine, methionine, proline, superoxide dismutase, silymarin, tea extracts, grape skin/seed extracts, melanin, and rosemary extracts.

The term "apply" as used herein refers to placing in contact with or to lay or spread on.

Arginine

As used herein, the phrase "arginine compound" is used to refer to arginine, its salt, conjugate, or analog thereof.

The term "arginine" is used herein to describe a molecule or compound that comprises one amino group, one guanidino group, and one carboxylic group. Arginine is a solid and a known irritant of the skin and the eyes. At physiological pH, the carboxylic acid is deprotonated (—COO⁻), the amino group is protonated (—NH$_3^+$), and the guanidino group is also protonated to give the guanidinium form (—C—(NH$_2$)$^{2+}$), making arginine a positively charged, aliphatic amino acid.

Arginine has the molecular formula $C_6H_{15}N_4O_2$ and may be generally depicted as shown in Formula I:

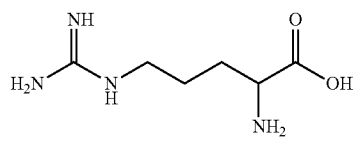

Formula I

According to some embodiments, the arginine compound may be in one or more isomeric forms as represented by Formulas II and III below.

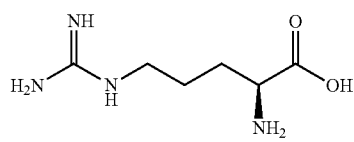

Formula II

L-Arginine

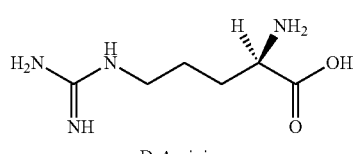

Formula III

D-Arginine

L-arginine, the enantiomer of D-arginine, is also known as L(+)-Arginine, (2S)-2-amino-5-(carbamimidamido)pentanoic acid, (2S)-2-amino-5-guanidinopentanoic acid, (S)-2-amino-5-guanidinopentanoic acid, and (S)-2-amino-5-guanidinovaleric acid. It is considered the physiologically active isomer of arginine. It plays a role in a number of essential biochemical processes. L-arginine is a conjugate base (meaning it contains one less H atom and one more negative charge than the acid that formed it) of L-arginium (1+) and a conjugate acid (meaning it contains one more H atom and one more positive charge than the base that formed it) of L-arginate.

D-arginine, the enantiomer of L-arginine, is also known as D-2-amino-5-guanidinovaleric acid, (2R)-2-amino-5-guanidinopentanoate. It believed that D-arginine may have properties slightly different from L-arginine (discussed supra). D-arginine is slightly soluble in water and is considered a moderately acidic compound based on its pKa. D-arginine is a conjugate base of a D-argininium(1+) and a conjugate acid of a D-argininate.

According to some embodiments, the arginine compound may be in one or more conjugate forms as represented by formulas IV and V below.

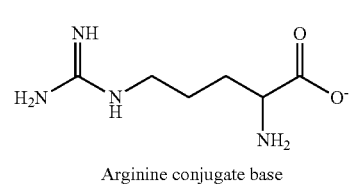

Formula IV

Arginine conjugate base

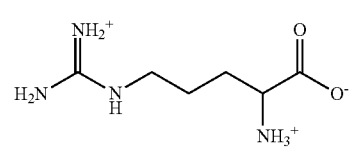

Formula V

Arginine conjugate acid

According to some embodiments, the arginine compound may be in one or more analog forms as represented by Formula VI:

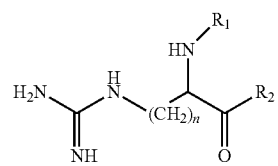

Formula VI wherein

R$_1$ represents a hydrogen atom, a hydroxyl group, an acyl or acyloxy radical, or an amino acid substituted or not on its free α-amino function, bound by a peptide bond;

R$_2$ represents a hydroxyl group, an amine, alkylamine or alcoxy radical, a silyloxy group, or an aminoacid substituted or not on its free α-carboxylic function, bound by a peptide bond; and n represent 3 or 4.

According to some embodiments, the arginine compound is obtained from a commercial source, including, but not limited to VladaChem, Tractus, Phion Ltd, MuseChem, MolPort, Sigma-Aldrich, LGC Standards, AN PharmaTech, ChemFaces, CAPOT, eNovation Chemicals, abcr GmbH, Tyger Scientific, Hairui Chemical, BLD Pharm, Biosynth, Aurum Pharmatech LLC, ApexBio Technology, ChemShuttle, Oakwood Products, DC Chemicals, AA BLOCKS, Yuhao Chemical, Norris Pharm, Tocris Bioscience, R&D Chemicals, Assembly Blocks Pvt. Ltd, Parchem, Angene Chemical, MedChemexpress MCE, Achemo Scientific Limited, Apexmol, Key Organics/BIONET, and the like. According to some embodiments, the arginine compound is synthesized.

The term "binding" and its other grammatical forms as used herein means a lasting attractive force between substances. The term "chemical bond" as used herein refers to an attractive force between atoms strong enough to permit the combined aggregate to function as a unit. The different principal types of bonds include metallic, covalent, ionic and bridge bonds. "Metallic bonding" is the attraction of all of the atomic nuclei in a crystal for the outer shell electrons, which are shared in a delocalized manner among all available orbitals. "Covalent bonding" results most commonly when electrons are shared by two atomic nuclei. A conventional single covalent bond involves the sharing of two elections. There also may be double bonds with four shared electrons, triple bonds with six shared elections, and bonds of intermediate multiplicity. Covalent bonds may range from nonpolar, involving electrons evenly shared by the two atoms, to extremely polar, where the bonding electrons are very unevenly shared. The limit of uneven sharing occurs when the bonding electron spends full time with one of the atoms, making the atom into a negative ion and leaving the other atom in the form of a positive ion. "Electrostatic (or ionic) bonding" is the electrostatic attraction between oppositely charged ions. "Bridge or hydrogen bonds" involve compounds of hydrogen in which the hydrogen bears either a + or a − charge.

The term "botanical raw material" as used herein refers to a fresh or processed (e.g., cleaned, frozen, dried, sliced or liquefied) part of a single species of plant or a fresh or processed alga or macroscopic fungus. The term "botanical ingredient" as used herein refers to a component that originates from a botanical raw material. The term "botanical product" refers to a finished labeled product that contains vegetable matter, which may include plant materials, algae, macroscopic fungi or a combination thereof. Depending in part on its intended use, a botanical product may be a food, drug or cosmetic. The term "botanical extract" as used herein refers to a product prepared by separating, by chemical or physical process, medicinally active portions of a plant from the inactive or inert components. The botanical extracts prepared according to some embodiments of the described invention may be obtained by means of a solvent, optionally under pressure and/or heat.

The term "intermolecule or non-bonded interactions," or "non-bonded forces," as used herein describe an attractive force that acts between atoms that is not a covalent bond. Such interactions may also be described as electrostatic interactions, which arise due to the unequal distribution of charge in a molecule, coulombic forces, intermolecular interactions and ionic interactions. Other "non-bonded interactions" include van der Waals force or dispersion, London, or London-Dispersion force, which is a weak electrostatic force created by momentary changes in a molecule's charge distribution; it is the weakness of all nonbonded forces on a per atom basis, which only operate over a very short distance range.

The term "carrier" as used herein describes a material that does not cause significant irritation to an organism and does not abrogate the biological activity and properties of the active compound of the composition of the described invention. Carriers must be of sufficiently high purity and of sufficiently low toxicity to render them suitable for administration to the mammal being treated. The carrier can be inert, or it can possess pharmaceutical benefits, cosmetic benefits or both. The terms "excipient", "carrier", or "vehicle" are used interchangeably to refer to carrier materials suitable for formulation and administration of pharmaceutically acceptable compositions described herein. Carriers and vehicles useful herein include any such materials know in the art which are nontoxic and do not interact with other components.

The term "conjugate acid-base pair" as used herein refers to a proton donor and its corresponding deprotonated species, e.g., benzoic acid (donor) and benzoate (acceptor). The term "conjugate acid" as used herein refers to the acid member of a pair of compounds that differ from each other by gain or loss of a proton. A conjugate acid can release or donate a proton. The term "conjugate base" as used herein refers to is the species that remains after the acid has donated its proton; a conjugate base can accept a proton.

Chemical Substituents

The term "aliphatic" as used herein, denotes a straight- or branched-chain arrangement of constituent carbon atoms, including, but not limited to paraffins (alkanes), which are saturated, olefins (alkenes or alkadienes), which are unsaturated, and acetylenes (alkynes), which contain a triple bond. In complex structures, the chains may be branched or cross-linked.

The term "lower" as used herein refers to a group having between one and six carbons.

The term "alkyl" as used herein refers to a straight or branched chain hydrocarbon having from 1 to 25 carbon atoms, optionally substituted with substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or S(O)$_2$ moieties. Examples of "alkyl" as used herein include, but are not limited to, methyl, ethyl, propyl, decyl, undecyl, octadecyl, nonadecyl, eicosyl, heneicosyl, decosyl, tricosyl, tetracosyl, and pentacosyl, n-butyl, t-butyl, n-pentyl, isobutyl, and isopropyl, and the like. According to some embodiments of the described invention, an analog comprises an alkyl of 1, 2, 3, 4, 5, 6, 7, 8, 9, 10, 11, or 12 carbon atoms.

The term "alkylene" as used herein refers to a straight or branched chain divalent hydrocarbon radical having from one to 25 carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or S(O)$_2$ moieties. Examples of "alkylene" as used herein include, but are not limited to, methylene, ethylene, and the like.

The term "alkenyl," as used herein, denotes a monovalent, straight (unbranched) or branched hydrocarbon chain having one or more double bonds therein where the double bond can be unconjugated or conjugated to another unsaturated group (e.g., a polyunsaturated alkenyl) and can be unsubstituted or substituted, with multiple degrees of substitution being allowed. It may be optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or $S(O)_2$ moieties. For example, and without limitation, the alkenyl can be vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, decenyl, undecenyl, dodecenyl, heptadecenyl, octadecenyl, nonadecenyl, eicosenyl, heneicosenyl, docosenyl, tricosenyl, tetracisenyl, pentacosenyl, phytyl, the branched chain isomers thereof, and polyunsaturated alkenes including octadec-9,12,-dienyl, octadec-9,12,15-trienyl, and eicos-5,8,11,14-tetraenyl.

The term "alkenylene" as used herein refers to a straight or branched chain divalent hydrocarbon radical having from 2 to 25 carbon atoms and one or more carbon-carbon double bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or $S(O)_2$ moieties. Examples of "alkenylene" as used herein include, but are not limited to, ethene-1,2-diyl, propene-1,3-diyl, methylene-1,1-diyl, and the like. Except where specifically indicated otherwise, any olefinic double bond of an alkenyl group that is capable of cis-trans isomerism may possess independently either the E or Z configuration.

The term "alkynyl" as used herein refers to a hydrocarbon radical having from 2 to 25 carbons and at least one carbon-carbon triple bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or $S(O)_2$ moieties.

The term "alkynylene" as used herein refers to a straight or branched chain divalent hydrocarbon radical having from 2 to 25 carbon atoms and one or more carbon-carbon triple bonds, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may contain one or more O, S, S(O), or $S(O)_2$ moieties. Examples of "alkynylene" as used herein include, but are not limited to, ethyne-1,2-diyl, propyne-1,3-diyl, and the like.

The term "aryl" as used herein refers to a benzene ring or to an optionally substituted benzene ring system fused to one or more optionally substituted benzene rings, with multiple degrees of substitution being allowed. Substituents include, but are not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-napthyl, 1-naphthyl, 1-anthracenyl, and the like.

It should be understood that wherever the terms "alkyl" or "aryl" or either of their prefix roots appear in a name of a substituent, they are to be interpreted as including those limitations given above for alkyl and aryl. Designated numbers of carbon atoms (e.g. $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, etc) shall refer independently to the number of carbon atoms in an alkyl, alkenyl or alkynyl or cyclic alkyl moiety or to the alkyl portion of a larger substituent in which the term "alkyl" appears as its prefix root.

The term "arylene" as used herein refers to a benzene ring diradical or to a benzene ring system diradical fused to one or more optionally substituted benzene rings, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

The terms "carbamates" or "urethanes" as used herein refer to a group of organic compounds sharing a common functional group having the general structure —NH(CO)O—.

The term "cycloalkyl" (used interchangeably with "aliphatic cyclic" herein) as used herein refers to a alicyclic hydrocarbon group optionally possessing one or more degrees of unsaturation, having from three to twelve carbon atoms, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and the like.

The term "cycloalkylene" as used herein refers to an non-aromatic alicyclic divalent hydrocarbon radical having from three to twelve carbon atoms and optionally possessing one or more degrees of unsaturation, optionally substituted with substituents selected from the group consisting of lower alkyl, lower alkoxy, lower alkyl sulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and the like.

The terms "heterocycle" and "heterocyclic" as used herein are used interchangeably to refer to a three to twelve-membered heterocyclic ring optionally possessing one or more degrees of unsaturation, containing one or more heteroatomic substitutions selected from –S—, —SO—, —SO$_2$—, —O—, or —N—, optionally substituted with substituents, including, but not limited to, lower alkyl, lower alkoxy, lower alkylsulfanyl, lower alkyl sulfenyl, lower alkyl sulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring optionally may be fused to one or more of another "heterocyclic" ring(s). Examples of "heterocyclic" include, but are not limited to, pyrrole, furan, thiophene, imidazole, oxazole, thiazole, pyrazole, 3-pyrroline, pyrrolidine, pyridine, pyrimidine, purine, quinoline, isoquinoline, carbazole and the like.

The term "C-linked heterocycle" means a heterocycle that is bonded through a carbon atom, e.g. —(CH2)$_n$-heterocycle where n is 1, 2 or 3 or —C<heterocycle where C<represents a carbon atom in a heterocycle ring. Similarly, R moieties that are N-linked heterocycles mean a heterocycle that is bonded through a heterocycle ring nitrogen atom, e.g. —N<heterocycle where N<represents a nitrogen atom in a heterocycle ring. A variable group such as an R moiety that is bonded to a Formula I compound, or a Formula II compound, can be a C-linked heterocycle or an N-linked heterocycle, These heterocycles include those listed below or described elsewhere herein.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, .beta.-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles can be bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at the nitrogen atom or position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or beta-carboline. Typically, nitrogen bonded heterocycles include 1-aziridyl, 1-azetedyl, 1-pyrrolyl, 1-imidazolyl, 1-pyrazolyl, and 1-piperidinyl and structures such as and tautomers of any of these.

The term "heterocyclylene" as used herein refers to a three to twelve-membered heterocyclic ring diradical optionally having one or more degrees of unsaturation containing one or more heteroatoms selected from S, SO, SO$_2$, O, or N, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more benzene rings or to one or more of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

The term "heteroaryl" as used herein refers to a five—to seven—membered aromatic ring, or to a polycyclic heterocyclic aromatic ring, containing one or more nitrogen, oxygen, or sulfur heteroatoms, where N-oxides and sulfur monoxides and sulfur dioxides are permissible heteroaromatic substitutions, optionally substituted with substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

The term "heteroarylene" as used herein refers to a five—to seven—membered aromatic ring diradical, or to a polycyclic heterocyclic aromatic ring diradical, containing one or more nitrogen, oxygen, or sulfur heteroatoms, where N-oxides and sulfur monoxides and sulfur dioxides are permissible heteroaromatic substitutions, optionally substituted with substituents including, but not limited to, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

The term "chiral" is used to describe asymmetric molecules that are nonsuperposable since they are mirror images of each other and therefore have the property of chirality. Such molecules are also called enantiomers and are characterized by optical activity.

The term "chirality" refers to the geometric property of a rigid object (or spatial arrangement of points or atoms) of being non-superposable on its mirror image; such an object has no symmetry elements of the second kind (a mirror plane, $\sigma = S1$, a center of inversion, $i = S2$, a rotation-reflection axis, S2n). If the object is superposable on its mirror image, the object is described as being achiral.

The term "chirality center" refers to an atom holding a set of ligands in a spatial arrangement, which is not superimposable on its mirror image. A chirality center may be considered a generalized extension of the concept of the asymmetric carbon atom to central atoms of any element.

The term "colorant" as used herein refers to a substance used to impart a color on a composition to improve the attractiveness of the composition and/or to enable easy product identification. Non-limiting examples of colorants include oil-soluble dyes, oil dispersible dyes, water-soluble dyes, e.g. acid blue 3, acid blue 104, acid green 1, acid green 25, acid yellow 3, acid yellow 73 sodium salt, D&C green No. 5, 6, & 8, D&C yellow No. 7, 8, 10, & 11, D&C violet No. 2, FD&C blue No. 1 & 2, FD&C green No. 3, FD&C yellow No. 5 & 6, and mixtures thereof.

The term "complex" as used herein refers to a molecular entity formed by a loose association involving two or more component molecular entities. The bonding between the components is normally weaker than in a covalent bond. The strength of the complex is derived from the delocalization and sharing of charges. A coordination complex (meaning a compound or ion with a central usually metallic atom or ion combined by coordinate bonds with a definite number of surrounding ions, groups, or molecules), also called a coordination compound, may or may not be covalent.

The term "component" as used herein refers to a constituent part, element or ingredient.

The term "contact" and its various grammatical forms as used herein refers to a state or condition of touching or of immediate or local proximity.

The term "cosmetic" as used herein refers to articles (excluding soap) intended to be rubbed, poured, sprinkled, or sprayed on, introduced into, or otherwise applied to the human body or any part thereof for cleansing, beautifying, promoting attractiveness, or altering the appearance, and articles intended for use as a component of any such articles.

The term "cosmetic composition" as used herein refers to a composition that is intended to be rubbed, poured, sprinkled, or sprayed on, introduced into, or otherwise applied to a subject or any part thereof for cleansing, beautifying, promoting attractiveness, or altering the appearance, or an article intended for use as a component of any such article, except that such term does not include soap.

The term "cosmetic effect" as used herein refers to a consequence of applying a cosmetic to the skin with the intention of improving is appearance or of beautifying it.

The term "cosmetically acceptable carrier" as used herein refers to a substantially non-toxic carrier, useable for administration of cosmetics, with which active compounds will remain stable and bioavailable. The carrier must be of sufficiently high purity and of sufficiently low toxicity to render it suitable for administration to the mammal being treated. It further should maintain the stability and bioavailability of an active agent. The cosmetically acceptable carrier is selected with the planned manner of administration in mind, to provide for the desired bulk, consistency, etc., when combined with an active agent and other components of a given composition.

The term "derivative" as used herein means a compound that may be produced from another compound of similar structure in one or more steps. A "derivative" or "derivatives" of a compound retains at least a degree of the desired function of the compound. Accordingly, an alternate term for "derivative" may be "functional derivative." Derivatives can include chemical modifications of the compound, such as akylation, acylation, carbamoylation, iodination or any modification that derivatizes the compound. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formal groups. Free carboxyl groups can be derivatized to form salts, esters, amides, or hydrazides. Free hydroxyl groups can be derivatized to form O-acyl or O-alkyl derivatives.

The term "dermatologic" as used herein refers to the branch of medicine that deals with the diagnosis and treatment of diseases and disorders of the skin.

The term "diastereoisomer" as used herein refers to stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-.

The terms "emollient" or "moisturizer" as used herein are used interchangeably to refer to complex mixtures of chemical agents specially designed to make the external layers of the skin (epidermis) softer and more pliable. An emollient increases the skin's hydration (water content) by reducing evaporation.

The term "enantiomer" as used herein refers to a pair of stereoisomers that are non-superimposable mirror images of each other. A 1:1 mixture of a pair of enantiomers is a "racemic" mixture. The term is used to designate a racemic mixture where appropriate.

The term "finished product" as used herein refers to a cosmetic composition that has undergone all stages of production, including packaging in its final container.

The terms "formulation" and "composition" are used interchangeably herein to refer to a product of the described invention that comprises all active and inert ingredients.

The term "fragrant" or "fragrances" as used herein refers to an aroma compound, also known as odorant, or flavorant, which is a chemical compound that has a smell or odor when it is sufficiently volatile to be transported to the olfactory system in the upper part of the nose. Generally molecules meeting this specification will have molecular weights of <300 g/mole. Flavors affect both the sense of taste and smell, whereas fragrances affect only smell. Generally, flavors tend to be naturally occurring, while fragrances tend to be synthetic. Aroma compounds can be found in food, wine, spices, perfumes, fragrance oils, and essential oils.

The term "hydrophilic" as used herein refers to a material or substance having an affinity for polar substances, such as water. The term "hydrophobic" as used herein refers to a material or substance having an affinity for nonpolar or neutral substances.

The term "hydrogen bond" as used herein refers to an attractive force, or bridge occurring in polar compounds in which a hydrogen atom of one molecule is attracted to two unshared electrons of another. Hydrogen bonds readily form between an electronegative atom (hydrogen acceptor, usually oxygen or nitrogen with a lone pair of electrons) and a hydrogen atom covalently bonded to another electronegative atom (the hydrogen donor) in the same or another molecule. Hydrogen bonds covalently bonded to carbon atoms (which are not electronegative) do not participate in hydrogen bonding. Hydrogen bonds are strongest when the bonded molecules are oriented to maximize electrostatic interaction, that is when the acceptor atom is in line with the covalent bond between the donor atom and H.

The term "hydroxy acids" (or polycarboxylic acids) as used herein refers to organic acids having one or more hydroxyl group attached directly to the carbon chain of an alphatic or alicyclic carbon atom. Alpha hydroxyl acids (AHAs) are water-soluble, and said to diminish fine skin lines and pigmentation spots and to stimulate collagen to allow the skin to repair itself. Examples include, without limitation, glycolic acid, lactic acid, tartaric acid, citric acid, malic acid, and mandelic acid. Beta hydroxyacids (BHAs) (e.g., salicylic acid) are lipid or oil-soluble; Hydroxy acids may be obtained from any commercial source or synthesized by any suitable methods. Exemplary synthesis methods are shown in Singh, Ram Sarup. Advances in Industrial Biotechnology. Chapter 4, Bhalla et al., "Hydroxy Acids: Productions and Applications." CI K International Publish, 2014.

As used herein the term "inflammation" refers to a physiologic response to infection and injury in which cells involved in detoxification and repair are mobilized to the compromised site by inflammatory mediators. The term "acute inflammation" as used herein, refers to inflammation, usually of sudden onset, characterized by the classical signs, with predominance of the vascular and exudative processes. The term "chronic inflammation" as used herein refers to inflammation of slow progress and marked chiefly by the formation of new connective tissue; it may be a continuation of an acute form or a prolonged low-grade form, and usually causes permanent tissue damage.

The term "isomer" as used herein refers to one of two or more molecules having the same number and kind of atoms and hence the same molecular weight, but differing in chemical structure. Isomers may differ in the connectivities of the atoms (structural isomers), or they may have the same atomic connectivities but differ only in the arrangement or configuration of the atoms in space (stereoisomers). Stereoisomers may include, but are not limited to, E/Z double bond isomers, enantiomers, and diastereomers. Structural moieties that, when appropriately substituted, can impart stereoisomerism include, but are not limited to, olefinic, imine or oxime double bonds; tetrahedral carbon, sulfur, nitrogen or phosphorus atoms; and allenic groups. Enantiomers are non-superimposable mirror images. A mixture of equal parts of the optical forms of a compound is known as a racemic mixture or racemate. Diastereomers are stereoisomers that are not mirror images. Stereoisomers can be synthesized in pure form (Nogradi, M.; Stereoselective Synthesis, (1987) VCH Editor Ebel, H. and Asymmetric Synthesis, Volumes 3-5, (1983) Academic Press, Editor Morrison, J.) or they can be resolved by a variety of methods such as crystallization and chromatographic techniques (Jaques, J.; Collet, A.; Wilen, S.; Enantiomer, Racemates, and Resolutions, 1981, John Wiley and Sons and Asymmetric Synthesis, Vol. 2, 1983, Academic Press, Editor Morrison, J). It will be recognized by those skilled in the art that the compounds of the described invention may contain chiral centers and as such may exist in different isomeric forms. The term "an optical isomer" or "a stereoisomer" as used herein refers to any of the various stereo isomeric configurations which may exist for a given compound of the present invention and includes geometric isomers. It is understood that a substituent may be attached at a chiral center of a carbon atom. Unless specified otherwise, the compounds of the present invention are meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. All tautomeric forms are also intended to be included. Tautomers are isomers of a compound which differ only in the position of the protons and electrons. The term "neutralize" as used herein refers to adding an acid to a basic solution or a base to an acidic solution until the resulting solution is chemically neutral (i.e., pH=7).

The term "nonpolar" as used herein refers to molecules or groups that are poorly soluble in water; hydrophobic. Nonpolar biomolecules interfere with water-water interactions but are unable to form water-solute interactions. In aqueous solutions, nonpolar molecules tend to cluster together. Nonpolar solvents such as chloroform and benzene are poor solvents for polar biomolecules, but easily dissolve those that are hydrophobic, e.g., nonpolar molecules, such as lipids and waxes.

The term "penetration" and its various grammatical forms as used herein refer to delivery of a substance through the skin.

The term "penetration enhancer" as used herein refers to an agent known to accelerate the delivery of a substance through the skin.

The term "percutaneous absorption" refers to the absorption of substances from outside the skin to positions beneath the skin, including into the blood stream. The epidermis of human skin is highly relevant to absorption rates. Passage through the stratum corneum marks the rate-limiting step for percutaneous absorption. The major steps involved in percutaneous absorption of, for example, a drug, include the establishment of a concentration gradient, which provides a driving force for drug movement across the skin, the release of drug from the vehicle into the skin-partition coefficient and drug diffusion across the layers of the skin-diffusion coefficient. The relationship of these factors to one another is summarized by the following equation:

$$J = C_{veh} \times K_m \cdot D/x \qquad \text{[Formula 1]}$$

where:
J=rate of absorption
$C_{veh}$=concentration of drug in vehicle
$K_m$=partition coefficient
D=diffusion coefficient There are many factors which affect the rate of percutaneous absorption of a substance. Primarily they are as follows: (i) Concentration. The more concentrated the substance, the greater the absorption rate; (ii) Size of skin surface area to which the drug is applied. The wider the contact area of the skin to which the substance is applied, the greater the absorption rate; (iii) Anatomical site of application. Skin varies in thickness in different areas of the body. A thicker and more intact stratum corneum decreases the rate of absorbency of a substance. The stratum corneum of the facial area is much thinner than, for example, the skin of the palms of the hands. The facial skin's construction and the thinness of the stratum corneum provide an area of the body that is optimized for percutaneous absorption to allow delivery of active agents both locally and systemically through the body; (iv) Hydration. Hydration (meaning increasing the water content of the skin) causes the stratum corneum to swell which increases permeability; (v) Increased skin temperature increases permeability; and (vi) The composition of the compound and of the vehicle also determines the absorbency of a substance. Most substances applied topically are incorporated into bases or vehicles. The vehicle chosen for a topical application will greatly influence absorption, and may itself have a beneficial effect on the skin. Factors that determine the choice of vehicle and the transfer rate across the skin are the substance's partition coefficient, molecular weight and water solubility. The protein portion of the stratum corneum is most permeable to water soluble substances and the liquid portion of the stratum corneum is most permeable to lipid soluble substances. It follows that substances having both liquid and aqueous solubility can traverse the stratum corneum more readily. See Dermal Exposure Assessment: Principles and Applications, EPA/600/8-91/011b, January 1992, Interim Report—Exposure Assessment Group, Office of Health and Environmental Assessment, U.S. Environmental Protection Agency, Washington, D.C. 20460. As used herein, the terms "occlude," "occluded," "occlusive" and the like refer to a transdermal formulation that is applied to the skin with the use of a supporting or otherwise associated structure. For example, a topical formulation may be applied to the skin of a subject with the aid of a structure, such as a backing member, bandage or cover. A matrix patch is an example of an occluded device. Conversely, the terms "unoccluded" and "non-occluded," which may be used interchangeably, refer to a transdermal formulation that is applied to the skin without the use of a support, backing member, cover or otherwise associated structure. For example, the transdermal formulation is applied to the skin in a free form, which is sufficient to effect transdermal delivery of the active agent without the use of structures, such as a backing member, etc. A gel formulation is an example of a non-occluded composition; other non-occluded compositions include ointments, lotions, pastes, mousses, aerosols and creams.

The term "peptide bond" is used herein to refer to a substituted amide linkage between an amino group of one chemical substance and the carboxyl group of another, with the elimination of the elements of water.

The term "pharmaceutical composition" is used herein to refer to a composition that is employed to prevent, reduce in intensity, cure or otherwise treat a target condition or disease.

The term "pharmaceutically acceptable," is used to refer to a carrier, diluent or excipient that is compatible with the other ingredients of the formulation or composition and not deleterious to the recipient thereof. The carrier must be of sufficiently high purity and of sufficiently low toxicity to render it suitable for administration to the subject being treated. The carrier further should maintain the stability and bioavailability of an active agent. For example, the term "pharmaceutically acceptable" can mean approved by a regulatory agency of the Federal or a state government or listed in the U.S. Pharmacopeia or other generally recognized pharmacopeia for use in animals, and more particularly in humans.

The term "polar" as used herein refers to molecules or groups that are soluble in water; hydrophilic. Polar biomolecules dissolve readily in water because they can replace water-water interactions with more energetically favorable water-solute interactions. Water, for example, is a polar solvent and forms hydrogen bonds with polar solutes. Uncharged but polar biomolecules, such as sugars, as well as alcohols, aldehydes, ketones and compounds containing amide bonds all form hydrogen bonds with water molecules and tend to be soluble in water.

The term "polymer" as used herein refers to any of various chemical compounds made of smaller, identical molecules (called monomers) linked together. Polymers generally have high molecular weights. The process by which molecules are linked together to form polymers is called "polymerization."

The term "preservative" as used herein refers to a substance that is added to a product to prevent decomposition by microbial growth or by undesirable chemical changes.

The term "reduce" or "reducing" as used herein refers to a diminution, a decrease, an attenuation, limitation or abatement of the degree, intensity, extent, size, amount, density, number or occurrence.

The term "salt bridge" as used herein refers to a non-covalent interaction between two ionized sites. A salt bridge has two components: a hydrogen bond and an electrostatic interaction. In one example of a salt bridge, a proton can migrates from a carboxylic acid group to the guanidine group in arginine.

The term "skin" as used herein refers to the largest organ in the body consisting of several layers. It plays an important role in biologic homeostasis, and is comprised of the epidermis and the dermis. The epidermis, which is composed of several layers beginning with the stratum corneum, is the outermost layer of the skin, and the innermost skin layer is the deep dermis. The skin has multiple functions, including thermal regulation, metabolic function (vitamin D metabolism), and immune functions.

In humans, the usual thickness of the skin is from 1-2 mm, although there is considerable variation in different parts of the body. The relative proportions of the epidermis and dermis also vary, and a thick skin is found in regions where there is a thickening of either or both layers. For example, on the interscapular (between the shoulder blades) region of the back, where the dermis is particularly thick, the skin may be more than 5 mm thick, whereas on the eyelids it may be less than 0.5 mm. Generally, the skin is thicker on the dorsal or extensor surfaces of the body than on the ventral or flexor surfaces; however, this is not the case for the hands and feet. The skin of the palms and soles is thicker than on any dorsal surface except the intrascapular region. The palms and soles have a characteristically thickened epidermis, in addition to a thick dermis The entire skin surface is traversed by numerous fine furrows, which run in definite directions and cross each other to bound small rhomboid or rectangular fields. These furrows correspond to similar ones on the surface of the dermis so that, in section, the boundary line between epidermis and dermis appears wavy. On the thick skin of the palms and soles, the fields form long, narrow ridges separated by parallel coursing furrows, and in the fingertips these ridges are arranged in the complicated loops, whorls (verticil) and spirals that give the fingerprints characteristic for each individual. These ridges are more prominent in those regions where the epidermis is thickest.

Where there is an epidermal ridge externally there is a corresponding narrower projection, called a "rete peg," on the dermal surface. Dermal papillae on either side of each rete peg project irregularly into the epidermis. In the palms and soles, and other sensitive parts of the skin, the dermal papillae are numerous, tall and often branched, and vary in height (from 0.05 mm to 0.2 mm). Where mechanical demands are slight and the epidermis is thinner, such as on the abdomen and face, the papillae are low and fewer in number.

The epidermis provides the body's buffer zone against the environment. It provides protection from trauma, excludes toxins and microbial organisms, and provides a semi-permeable membrane, keeping vital body fluids within the protective envelope. Traditionally, the epidermis has been divided into several layers, of which two represent the most significant ones physiologically. The basal-cell layer, or germinative layer, is of importance because it is the primary source of regenerative cells. In the process of wound healing, this is the area that undergoes mitosis in most instances. The upper epidermis, including stratum and granular layer, is the other area of formation of the normal epidermal-barrier function.

The stratum corneum is an avascular, multilayer structure that functions as a barrier to the environment and prevents transepidermal water loss. Recent studies have shown that enzymatic activity is involved in the formation of an acid mantle in the stratum corneum. Together, the acid mantle and stratum corneum make the skin less permeable to water and other polar compounds, and indirectly protect the skin from invasion by microorganisms. Normal surface skin pH is between 4 and 6.5 in healthy people; it varies according to area of skin on the body. This low pH forms an acid mantle that enhances the skin barrier function.

Other layers of the epidermis below the stratum corneum include the stratum lucidum, stratum *granulosum*, stratum germinativum, and stratum basale. Each contains living cells with specialized functions. For example melanin, which is produced by melanocytes in the epidermis, is responsible for the color of the skin. Langerhans cells are involved in immune processing.

Dermal appendages, which include hair follicles, sebaceous and sweat glands, fingernails, and toenails, originate in the epidermis and protrude into the dermis hair follicles and sebaceous and sweat glands. They contribute epithelial cells for rapid reepithelialization of wounds that do not penetrate through the dermis (termed partial-thickness wounds). The sebaceous glands are responsible for secretions that lubricate the skin, keeping it soft and flexible. They are most numerous in the face and sparse in the palm of the hands and soles of the feet. Sweat gland secretions control skin pH to prevent dermal infections. The sweat glands, dermal blood vessels, and small muscles in the skin (responsible for goose pimples) control temperature on the surface of the body. Nerve endings in the skin include receptors for pain, touch, heat, and cold. Loss of these nerve endings increases the risk for skin breakdown by decreasing the tolerance of the tissue to external forces.

The basement membrane both separates and connects the epidermis and dermis. When epidermal cells in the basement membrane divide, one cell remains, and the other migrates through the granular layer to the surface stratum corneum. At the surface, the cell dies and forms keratin. Dry keratin on the surface is called scale. Hyperkeratosis (thickened layers of keratin) is found often on the heels and indicates loss of sebaceous gland and sweat gland functions if the patient is diabetic. The basement membrane atrophies with aging; separation between the basement membrane and dermis is one cause for skin tears in the elderly.

The dermis, or the true skin, is a vascular structure that supports and nourishes the epidermis. In addition, there are sensory nerve endings in the dermis that transmit signals regarding pain, pressure, heat, and cold. The dermis is divided into two layers: the superficial dermis and the deep dermis.

The superficial dermis consists of extracellular matrix (collagen, elastin, and ground substances) and contains blood vessels, lymphatics, epithelial cells, connective tissue, muscle, fat, and nerve tissue. The vascular supply of the dermis is responsible for nourishing the epidermis and regulating body temperature. Fibroblasts are responsible for producing the collagen and elastin components of the skin that give it turgor. Fibronectin and hyaluronic acid are secreted by the fibroblasts. The structural integrity of the dermis plays a role in the normal function and youthful appearance of the skin.

The deep dermis is located over the subcutaneous fat; it contains larger networks of blood vessels and collagen fibers to provide tensile strength. It also consists of fibroelastic connective tissue, which is yellow and composed mainly of collagen. Fibroblasts are also present in this tissue layer. The well-vascularized dermis withstands pressure for longer periods of time than subcutaneous tissue or muscle. The collagen in the skin gives the skin its toughness. Dermal wounds, e.g., cracks or pustules, involve the epidermis, basal membrane, and dermis. Typically, dermal injuries heal rapidly.

Substances are applied to the skin to elicit one or more of four general effects: an effect on the skin surface, an effect within the stratum corneum; an effect requiring penetration into the epidermis and dermis; or a systemic effect resulting from delivery of sufficient amounts of a given substance through the epidermis and the dermis to the vasculature to produce therapeutic systemic concentrations.

As used herein, the term "solidify" refers to the physical and/or chemical alteration of a liquid base material so as to form a solid or semi-solid at ambient conditions. According to some embodiments, it means to form a final composition that has a stable physical structure and can be deposited on the skin under normal use conditions.

The terms "soluble" and "solubility" refer to the property of being susceptible to being dissolved in a specified fluid (solvent). The term "insoluble" refers to the property of a material that has minimal or limited solubility in a specified solvent. In a solution, the molecules of the solute (or dissolved substance) are uniformly distributed among those of the solvent.

According to the European Pharmacopoeia, the solubility of a compound in water in the range of 15° C. to 25° C. is defined as follows:

|  | Solvent in mL per gram compound |
| --- | --- |
| Very readily soluble | <1 |
| Readily soluble | from 1 to 10 |
| Soluble | from >10 to 30 |
| Hardly soluble | from >30 to 100 |
| Poorly soluble | from >100 to 1,000 |
| Very poorly soluble | from >1,000 to 10,000 |
| Water-insoluble | >10,000 |

The term "solubilizing agents" as used herein refers to those substances that enable solutes to dissolve.

A "solution" generally is considered as a homogeneous mixture of two or more substances. It is frequently, though not necessarily, a liquid. In a solution, the molecules of the solute (or dissolved substance) are uniformly distributed among those of the solvent.

The term "solvate" as used herein refers to a complex formed by the attachment of solvent molecules to that of a solute.

The term "solvent" as used herein refers to a substance capable of dissolving another substance (termed a "solute") to form a uniformly dispersed mixture (solution).

The term "stable" and its various grammatical forms as used herein refers to the capability of a particular formulation to remain within its physical, chemical, microbiological, therapeutic and toxicological specifications.

The term "stabilizer" as used herein refers to a chemical which tends to inhibit the reaction between two or more other chemicals.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., Stereochemistry of Organic Compounds (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

The term "substituted" as used herein refers to replacement of an element or radical with another, multiple degrees of substitution being allowed unless otherwise stated.

The term "surfactant" or "surface active agent" as used herein refers to a compound that lowers the surface tension (or interfacial tension) between two liquids or between a liquid and a solid.

The term "suspension" as used herein refers to a dispersion (mixture) in which a finely-divided species is combined with another species, with the former being so finely divided and mixed that it doesn't rapidly settle out. In everyday life, the most common suspensions are those of solids in liquid.

The term "synergistic effect" as used herein, refers to a combined effect of two chemicals, which is greater than the sum of the effect of each agent alone.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation.

The terms "therapeutic amount", "cosmetic amount" or an "amount effective" of one or more of the active agents as used herein refer to an amount that is sufficient to provide the intended benefit of treatment.

The term "thickening agent" or "viscoscity increasing agent" refers to a substance that can increase the viscosity of a liquid without substantially changing its other properties.

The term "thinning agent" as used herein refers to a substance that reduces the viscosity of a liquid making it easier to apply.

The term "treat" or "treating" includes abrogating, substantially inhibiting, slowing or reversing the progression of a disease, condition or disorder, substantially ameliorating clinical or esthetic symptoms of a condition, substantially preventing the appearance of clinical or esthetic symptoms of a disease, condition, or disorder, and protecting from harmful or annoying symptoms. Treating further refers to accomplishing one or more of the following: (a) reducing the severity of the disorder; (b) limiting development of symptoms characteristic of the disorder(s) being treated; (c) limiting worsening of symptoms characteristic of the disorder(s) being treated; (d) limiting recurrence of the disorder(s) in subjects that have previously had the disorder(s); and (e) limiting recurrence of symptoms in subjects that were previously asymptomatic for the disorder(s).

The term "topical" as used herein refers to administration of an inventive composition at, or immediately beneath, the point of application. The term "topical administration" and "topically applying" as used herein are used interchangeably to refer to delivering a composition onto one or more surfaces, including epithelial surfaces. The composition may be applied by pouring, dropping, or spraying, if a liquid; rubbing on, if an ointment, lotion, cream, gel, or the like; dusting, if a powder; spraying, if a liquid or aerosol composition; or by any other appropriate means. Topical administration generally provides a local rather than a systemic effect.

The term "viscosity", as used herein refers to the property of a fluid that resists the force tending to cause the fluid to flow. The resistance is caused by intermolecular friction exerted when layers of fluids attempt to slide by one another. Viscosity can be of two types: dynamic (or absolute) viscosity and kinematic viscosity. Absolute viscosity or the coefficient of absolute viscosity is a measure of the internal resistance. Dynamic (or absolute) viscosity is the tangential force per unit area required to move one horizontal plane with respect to the other at unit velocity when maintained a unit distance apart by the fluid. Dynamic viscosity is usually denoted in poise (P) or centipoise (cP), wherein 1 poise=1 g/cm$^2$, and 1 cP=0.01 P. Kinematic viscosity is the ratio of absolute or dynamic viscosity to density. Kinematic viscosity is usually denoted in Stokes (St) or Centistokes (cSt), wherein 1 St=10-4 m$^2$/s, and 1 cSt=0.01 St.

Volume/volume percentage (v/v percent) is a measure of the concentration of a substance in a solution. It is expressed as the ratio of the volume of the solute to the total volume of the solution multiplied by 100.

The term "wetting agent" as used herein refers to a substance that reduces the surface tension of water in order to allow it to spread drops onto a surface, thereby increasing the spreading abilities of a liquid. Wetting agents aid in attaining intimate contact between solid particles and liquids. There are four main types of wetting agents: anionic, cationic, amphoteric and nonionic. Anionic, cationic and amphoteric wetting agents ionize when mixed with water. Surfactants, for example, are also wetting agents that reduce the contact angle between a solution put on a surface and the surface. This property allows surfactants to spread more easily on the surface and inject themselves between an oily deposit and the skin or hair surface. This lifts up the oil and allows it to be removed. Wetting, which is useful in cosmetic creams and lotions, also makes the product easier to spread and prevents it from balling up on the surface.

The term "wound healing" or "wound repair" as used herein refers generally to the body's natural process of regenerating dermal or epidermal tissue. When an individual is wounded, a set of complex biochemical events takes place to repair the damage including, hemostasis, inflammation, proliferation, and remodeling.

The term "wound healing agent" as used herein refers to an agent that promotes an intricate process where the skin or other body tissue repairs itself after injury. In normal skin, the epidermis (surface layer) and dermis (deeper layer) form a protective barrier against the external environment. As such, the term "wound healing agent" refers to any substance that facilitates the wound healing process.

As used herein, a "wt %" or "weight percent" or "percent by weight" or "wt/wt %" of a component, unless specifically stated to the contrary, refers to the ratio of the weight of the component to the total weight of the composition in which the component is included, expressed as a percentage.

Formulations

According to some embodiments, the described invention provides a cosmetic composition stabilizing system comprising an effective amount of an arginine component. According to some embodiments, the arginine component comprises i) arginine, or a conjugate, or an analog thereof, ii) an organic acid, a conjugate, or an analog thereof, and iii) a solvent. As used herein, the phrase "arginine, a conjugate, or an analog thereof" is referred to as an "arginine compound." As used herein, the phrase "organic acid, a conjugate, or a derivative thereof" is referred to as an "organic acid compound." According to some embodiments the arginine component comprises i) an arginine compound, ii) an organic acid compound, and iii) a solvent.

According to some embodiments, the described invention further provides methods and formulations for preparing stable cosmetic compositions comprising the cosmetic composition stabilizing system comprising an effective amount of the arginine component, an acceptable carrier, and optionally an active agent. According to some embodiments, the arginine component comprises i) arginine, or a conjugate, or an analog thereof, ii) an organic acid, a conjugate, or a derivative thereof, and iii) a solvent. As used herein, the phrase "arginine, a conjugate, or an analog thereof" is referred to as an "arginine compound." As used herein, the phrase "organic acid, a conjugate, or derivative thereof" is referred to as an "organic acid compound." According to some embodiments the arginine component comprises i) an arginine compound, ii) an organic acid compound, and iii) a solvent.

According to some embodiments, the described invention provides topical cosmetic or dermatologic compositions comprising an effective amount of an arginine component, a cosmetically acceptable carrier or pharmaceutically acceptable carrier, and optionally one or more active agents. Forms of topical compositions include occluded forms, such as matrix and reservoir patches, and unoccluded forms, such as gels, creams, lotions, ointments, emulsions, serums, foams, aerosols, and mousses.

Arginine Component

According to some embodiments, the arginine component has a singular effect, meaning one therapeutic or cosmetic effect. According to some embodiments, the arginine component has a multifunctional effect. According to some embodiments, the cosmetic composition stabilizing system has a synergistic effect with the active agent. According to some embodiments, the cosmetic composition stabilizing system has a preservative effect on the composition, a solubilizing effect, a stabilizing, a neutralizing, or anti-microbial effect on the composition, and a moisturizing, anti-aging (meaning an effect where the skin looks healthier and if possible younger than it actually is; an effect that hides, reduces, or prevent skin sagging, skin wrinkles, or skin roughness), anti-wrinkle (smoothing or lessening the appearance of fine lines of the skin), exfoliating (meaning a technique where dead cells are removed from the top layer of the skin, which helps to brighten the complexion, and lets skin-care products penetrate deeper into the skin), and/or healing effect, or any combination thereof. For example, according to some embodiments the cosmetic composition stabilizing system has a preservative effect on the composition and/or a solubilizing effect on the active agent. According to some embodiments the cosmetic composition stabilizing system has a preservative effect on the composition, and/or a solubilizing effect on the active agent, and/or a stabilizing effect on the composition. According to some embodiments, the cosmetic composition stabilizing system has a preservative effect on the composition, and/or a solubilizing effect on the active agent, and/or a stabilizing effect and/or a neutralizing effect on the composition. According to some embodiments, the cosmetic composition stabilizing system has a preservative effect on the composition, and/or a solubilizing effect on the active, and/or a stabilizing, neutralizing, and/or anti-microbial effect on the composition. According to some embodiments, the cosmetic composition stabilizing system has a preservative effect on the composition, and/or a solubilizing effect on the active, a stabilizing, and/or a neutralizing, and/or an anti-microbial effect on the composition, and/or an anti-aging cosmetic/therapeutic effect. According to some embodiments, the cosmetic composition stabilizing system has a preservative effect on the composition, a solubilizing effect on the active, and/or a stabilizing, a neutralizing, and/or an anti-microbial effect on the composition and/or an anti-aging, and moisturizing cosmetic/therapeutic effect. According to some embodiments, the cosmetic composition stabilizing system has a preservative effect on the composition, and/or a solubilizing effect on the active, a stabilizing, neutralizing, and/or anti-microbial effect on the composition, and/or an anti-aging, moisturizing, and/or anti-wrinkle cosmetic/therapeutic effect. According to some embodiments, the cosmetic composition stabilizing system has a preservative effect on the composition, and/or a solubilizing effect on the active, and/or a stabilizing, a neutralizing, and/or an anti-microbial effect on the composition, and/or an anti-aging, moisturizing, anti-wrinkle, and/or exfoliating cosmetic/therapeutic effect. According to some embodiments, the cosmetic composition stabilizing system has a preservative effect on the composition, and/or a solubilizing, stabilizing, neutralizing, and/or anti-microbial effect on the composition, and/or an anti-aging, moisturizing, anti-wrinkle, exfoliating and/or healing cosmetic/therapeutic effect.

According to some embodiments, the arginine component of the cosmetic composition stabilizing system comprises i) an arginine compound, ii) an organic acid compound, and iii) a solvent. According to some embodiments, the arginine component comprises an arginine-organic acid complex comprising i) the arginine compound and ii) the organic acid compound, in iii) the solvent. According to some embodiments, the arginine-organic acid complex is formed through non-bonded interactions. According to some embodiments, the non-bonded interactions are hydrogen bonds. According to some embodiments, the non-bonded interactions are salt bridges.

According to some embodiments, the arginine compound is arginine, or a salt, conjugate, or analog thereof. For example, the arginine may be D,L-arginine, D-arginine, L-arginine, alkyl (ethyl, methyl, propyl, isopropyl, butyl, isobutyl, t-butyl) esters of arginine and conjugates and analogs thereof.

According to some embodiments, the arginine conjugate may be a conjugate acid or a conjugate base. For example, the argine conjugate may be argininum, or argininate.

According to some embodiments, the arginine compound may be employed in any suitable amount. For example, the arginine compound may be present in the arginine component in at least about 1.0 wt %, at least about 5.0 wt %, at least 10.0 wt %, at least about 15.0 wt %, at least 20.0 wt %, at least 25.0 wt %, at least 30.0 wt %, at least 35.0 wt %, at least 40.0 wt %, at least 45.0 wt %, at least 50.0 wt %, at least 55.0 wt %, at least 60.0 wt %, at least 65.0 wt %, at least 70.0 wt %, at least 75.0 wt %, at least 80.0 wt %, at least 85.0 wt %, at least 90.0 wt %, and about 95.0 wt % of the total weight of the arginine component. Exemplary amounts include 10.0 wt % to about 70.0 wt %, inclusive, based upon the total weight of the arginine component, about 20 wt % to about 60 wt % inclusive, based upon the total weight of the arginine component, about 30 wt % to about 50 wt % inclusive of the total weight of the arginine component.

According to some embodiments, the organic acid compound can be an organic acid, its conjugate, or an analog thereof. According to some embodiments the organic acid can be any suitable organic acid. For example, organic acids may be substituted and non-substituted aliphatic (saturated and unsaturated) and aromatic acids. Organic acids may possess as substituents one or more functional groups, such as alkyl, alkenyl, alkynyl, halogen, hydroxy, carbonyl, carboxylic acid, aldehyde, ester, amide, carbonate, carbamate, ether, amino, cyano, isocyano, oxy, oxo, thia, aza, azide, imine, nitro, nitrate, nitroso, nitrosooxy, cyanate, isocyanate, thiocyanate, isothiocyanate, sulfinyl, sulfhydryl, sulfonyl, phosphino, wherein each of the alkyl, alkenyl, alkynyl and amino groups may themselves be optionally substituted with one or more of the preceding functional groups. According to some embodiments, some functional groups, such as hydroxy, will impart or augment a character to the acid that is suitable for the present composition, such as a hygroscopic character. According to some embodiments, the organic acid contains multiple carboxylic acid groups.

According to some embodiments, the organic acid is a hydroxy acid. According to some embodiments, the hydroxy acid is an α-hydroxy acid (AHA), a β-hydroxy acid (BHA), a γ-Hydroxy acids (GBA), an ω-Hydroxy acids, a monohydroxy acid (MHA), a polyhydroxy acid (PHA)/polycarboxy hydroxy acid (PCHA), an aliphatic hydroxy acid (AlHA), an aromatic hydroxy acids acid (ArHAs), an arylaliphatic hydroxy acid (AAHA), a hydroxy fatty acids, and the like.

According to some embodiments, the hydroxy acid is an α-hydroxy acid (AHA). The alpha (α) carbon in organic molecules refers to the first carbon atom that attaches to a functional group, such as a carbonyl. According to some embodiments, the AHA is an alkyl AHA, arylalkyl AHA, or a polycarboxyl AHA.

According to some embodiments, an alkyl AHA comprises a hydroxyl group attached at the α carbon of an alkyl carbon chain of hydrocarbons. Examples of alkyl AHAs are shown in Table 2 below. (Taken from Singh, Ram Sarup. Advances in Industrial Biotechnology. Chapter 4, Bhalla et al., "Hydroxy Acids: Productions and Applications." CI K International Publish, 2014).

TABLE 2

Alkyl α-hydroxy acids.

| Common name | Structure formula | Systematic name |
|---|---|---|
| Glycolic acid | $CH_2OHCOOH$ | α-Hydroxyethanoic acids |
| Lactic acid | $CH_3 CHOHCOOH$ | α-Hydroxypropanoic acid |
| Methyl lactic acid | $(CH_3)_2COHCOOH$ | α-Methyl,α-hydroxpropanoic acid |
| α-Hydroxybutyric acid | $CH_3CH_2 CHOHCOOH$ | α-Hydroxybutanoic acid |
| DL-α-Hydroxy valeric acid | $CH_3(CH_2)_2CHOHCOOH$ | α-Hydroxypentanoic acid |
| DL-α-Hydroxy caproic acid | $CH_3,(CH_2)_3CHOHCOOH$ | α-Hydroxyhexanoic acid |
| α-Hydroxy enanthoic acid | $CH_3,(CH_2)_4CHOHCOOH$ | α-Hydroxyheptanoic acid |
| α-Hydroxy caprylic acid | $CH_3(CH_2)_5CHOHCOOH$ | α-Hydroxyoctanoic acid |
| α-Hydroxy pelargonic acid | $CH_3(CH_2)_6CHOHCOOH$ | α-Hydroxynonanoic acid |
| α-Hydroxy capric acid | $CH_3(CH_2)_7CHOHCOOH$ | α-Hydroxydecanoic acid |
| α-Hydroxy hendecanoic acid | $CH_3(CH_2)_8CHOHCOOH$ | α-Hydroxyundecanoic acid |
| α-Hydroxy lauric acid | $CH_3(CH_2)_9CHOHCOOH$ | α-Hydroxydodecanoic acid |
| α-Hydroxy myristic acid | $CH_3(CH_2)_{11}CHOHCOOH$ | α-Hydroxytetradecanoi |
| α-Hydroxy palmitic acid | $CH_3(CH_2)_{13}CHOHCOOH$ | α-Hydroxyhexadecanoic acid |
| DL-α-Hydroxy stearic acid | $CH_3(CH_2)_{15}CHOHCOOH$ | α-Hydroxyoctadecanoic acid |
| Cerebronic acid | $CH_3(CH_2)_{21}CHOH—COOH$ | α-Hydroxytetraeicosanoic acid |

According to some embodiments, an arylalkyl AHA comprises a phenyl group attached to the alpha-carbon of the alkyl AHA. According to some embodiments, examples of arylalkyl AHAs are as in Table 3 below. (Taken from Singh, Ram Sarup. Advances in Industrial Biotechnology. Chapter 4, Bhalla et al., "Hydroxy Acids: Productions and Applications." CI K International Publish, 2014).

TABLE 3

Arylalkyl alpha-hydroxy acids

| Common name | Chemical structure | Systematic name |
|---|---|---|
| Mandelic acid | $C_8H_8O_3$ | 2-Phenyl α-hydroxyethanoic acid |
| Benzilic acid | $C_{14}H_{12}O_3$ | 2,2-Diphenyl α-hydroxyethanoic acid |
| Phenyllactic acid | $C_9H_{10}O_3$ | 3-Phenyl α-hydroxypropanoic acid |
| Atrolactic acid | $C_{10}H_{12}O_2$ | 2-Phenyl 2-methyl α-hydroxyethanoic acid |

According to some embodiments, the hydroxy acid is a β-hydroxy acid (BHA). A BHA is a carboxylic acid having one hydroxyl group attached to the second carbon atom that attaches to a functional group, such as a carbonyl in the β-position According to some embodiments, BHAs may include 3-hydroxypropanoic acid (β-hydroxypropanoic acid), 3-hydroxybutanoicacid (β-hydroxybutyric acid), 4, 2-phenyl-3-hydroxypropanoic acid (tropic acid), 3-hydroxy-3,7,11-trimethyldodecanoic acid and 9,10,16-trihydrohexadecanoicacid (aleuratic acid).

According to some embodiments, the hydroxy acid is a polyhydroxy acid or a polycarboxy hydroxy acid (PHA/PCHA). A PHA is a carboxylic acid with two or more hydroxyl groups attached to carbon atoms or an alicyclic chain wherein at least one hydroxyl group is attached to the α-position.

According to some embodiments, a PHA may include the examples in Table 4. (Taken from Singh, Ram Sarup. Advances in Industrial Biotechnology. Chapter 4, Bhalla et al., "Hydroxy Acids: Productions and Applications." CI K International Publish, 2014).

TABLE 4

Polyhydroxy acids.

| Common name | Sstructure formula | Systematic name |
|---|---|---|
| Glyceric acid | $HOCH_2CHOHCOOH$ | 2,3-Dihydroxypropanoic acid |
| Erythronic acid, threonic acid | $HOCH_2(CHOH_3)COOH$ | 2,3,4-Trihydroxybutanoic acid |
| Ribonic acid, arabionic acid, xylonic acid | $HOCH_2(CHOH)_4COOH$ | 2,3,4,5-Tetrahydroxypentanoic acid |
| Allonic acid, altonic acid, gluconic acid | $HOCH_2(CHOH)_5COOH$ | 2,3,4,5,6-Pentahydroxyhexanoic acid |
| Allheptnoic acid, altroheptnoic acid, glucoheptonic acid | $HOCH_2(CHOH)_6COOH$ | 2,3,4,5,6,7-Hexahydroxyheptanoic acid |

According to some embodiments, a PCHA is an AHA that has more than one carboxyl group. According to some embodiments, some examples of a PCHA are as included in Table 5 below. (Taken from Singh, Ram Sarup. Advances in Industrial Biotechnology. Chapter 4, Bhalla et al., "Hydroxy Acids: Productions and Applications." CI K International Publish, 2014).

TABLE 5

Polycarboxy hydroxy acids.

| Common name | Structure | Systematic name |
|---|---|---|
| Tartonic acid | $HOOCCHOHCOOH$ | 2-Hydroxypropane-1,3-dioic acid |
| Malic acid | $HOOCCH_2CHOHCOOH$ | 2-Hydroxybutane-1,4-dioic acid |
| Citramalic acid | $HOOCCH_2C(CH_3)OHCOOH$ | 2-Hydroxy-2-methylbutane-1,4-dioic acid |
| Tartaric acid | $HOOCCHOHCHOHCOOH$ | 2,3-Dihydroxybutane-1,4-dioic acid |
| Citric acid | $C(OH)(COOH)(CH_2COOH)_2$ | 3-Carboxy-3-hydroxypentane 1,5-dioic acid |
| Isocitric acid | $HOOCCH_2OHCH(COOH)CH_2COOH$ | 3-Carboxy-2-hydroxypentane 1,5-dioic acid |
| Homocitric acid | $HOOCCH_2(OH)(COOH)(CH_2)_2COOH$ | 3-Carboxy-3-hydroxyhexane 1,6-dioic acid |
| Homoisocitric acid | $HOOCCHOHCH(COOH)(CH_2)_2COOH$ | 3-Carboxy-2-hydroxyhexane 1,6-dioic acid |

According to some embodiments, an ArHA is also known as phenocarboxylic acids. According to some embodiments, an ArHA contains a phenolic ring and carboxylic acid functional group, and at least one hydroxy group wherein at least one hydroxy group is attached to the ring. According to some embodiments, examples of ArHAa are shown in Table 6 below. (Taken from Singh, Ram Sarup. Advances in Industrial Biotechnology. Chapter 4, Bhalla et al., "Hydroxy Acids: Productions and Applications." CI K International Publish, 2014).

TABLE 6

Aromatic hydroxy acids

| Common name | Structure formula | Systematic name |
|---|---|---|
| o-Coumaric acid | $C_9H_8O_3$ | (E)-3-(2-hydroxyphenyl)prop-2-enoic acid |
| p-Coumaric acid | $C_9H_8O_3$ | (E)-3-(4-Hydroxyphenyl)-2-propenoic acid |
| m-Coumaric acid | $C_9H_8O_3$ | (E)-3-(3-Hydroxyphenyl)-2-propenoic acid |
| Ferulic acid | $C_{10}H_{10}O_4$ | (E)-3-(4-Hydroxy-3-methoxy-phenyl) prop-2-enoic acid |
| Sinapic acid | $C_{11}H_{12}O_5$ | 3-(4-Hydroxy-3,5-dimethoxyphenyl prop-2-enoic acid |
| Caffeic acid | $C_9H_8O_4$ | 3-(3,4-Dihydroxyphenyl 2-propenoic acid |
| Salicylic acid | $C_7H_6O_3$ | 2-Hydroxybenzoic acid |
| m-Hydroxybenzoic acid | $C_7H_6O_3$ | 3-Hydroxybenzoic acid |
| p-Hydroxybenzoic acid | $C_7H_6O_3$ | 4-Hydroxybenzoic acid |
| Vanillic acid | $C_8H_8C_4$ | 4-Hydroxy-3-methoxybenzoic acid |
| Syringic acid | $C_9H_{10}O_5$ | 4-Hydroxy-3,5-dimethoxybenzoic acid |
| Protocatechuic acid | $C_7H_6O_4$ | 3,4-Dihydroxybenzoic acid |
| Gentisic acid | $C_7H_6O_4$ | 2,5-Dihydroxybenzoic acid |
| Gallic acid | $C_7H_6O_5$ | 3,4,5-Trihydroxybenzoic acid |
| Phloroglucinol carboxylic acid | $C_7H_6O_5$ | 2,4,6-Trihydroxybenzoic acid |

According to some embodiments, the organic acid component comprises anisic acid, also known as 2-methoxybenzoic acid; o-Anisic acid; 579-75-9; o-Methoxybenzoic acid; 2-Anisic acid; O-Methylsalicylic acid; Benzoic acid, 2-methoxy-; Salicylic acid methyl ether; 2-Methoxy-benzoic acid; 529-75-9, molecular formula $C_8H_8O_3$.

According to some embodiments, the organic acid component comprises levulinic acid also known as 4-Oxopentanoic acid; 123-76-2; Laevulinic acid; Pentanoic acid, 4-oxo-4-Oxovaleric acid; Levulic acid; 3-Acetylpropionic acid; 4-Ketovaleric acid; LEVA; molecular formula $C_5H_8O_3$.

According to some embodiments, the organic acid component comprises mandelic acid, also known as 17199-29-0; (S)-(+)-Mandelic acid; (S)-Mandelic acid; (S)-2-Hydroxy-2-phenylacetic acid; L-mandelic acid; L-(+)-mandelic acid; S-(+)-Mandelic acid; (2S)-2-hydroxy-2-phenylacetic acid; UNII-LOUMW58G3T; 1(+)-mandelic acid; molecular formula $C_8H_8O_3$.

According to some embodiments, the organic acid component comprises salicylic acid, also known as 2-Hydroxybenzoic acid; 69-72-7; o-hydroxybenzoic acid; 2-Carboxyphenol; o-Carboxyphenol; Rutranex; Salonil; Retarder W; Keralyt, molecular formula C7H6O3 or $HOC_6H_4COOH$.

According to some embodiments, the organic acid component comprises sorbic acid, also known as 110-44-1; 2,4-Hexadienoic acid; (2E,4E)-hexa-2,4-dienoic acid; 2E,4E-Hexadienoic acid; Panosorb; Sorbistat; 2-Propenylacrylic acid; trans, trans-Sorbic acid; Hexadienoic acid, molecular formula $C_6H_8O_2$ or $CH_3CH=CHCH=CHCOOH$.

According to some embodiments, the organic acid component comprises benzoic acid, also known as 65-85-0; Dracylic acid; benzenecarboxylic acid; Carboxybenzene; Benzeneformic acid; phenylformic acid; Benzenemethanoic acid; Phenylcarboxylic acid; Retardex, molecular formula $C_7H_6O_2$ or $C_6H_5COOH$.

According to some embodiments, the organic acid component comprises ferulic acid, also known as trans-4-Hydroxy-3-methoxycinnamic acid, and trans-Ferulic acid, molecular formula $HOC_6H_3(OCH_3)CH=CHCO_2H$.

According to some embodiments, the organic acid component comprises syringic acid, also known as 3,5-Dimethoxy-4-hydroxybenzoic acid, 4-Hydroxy-3,5-dimethoxybenzoic acid, and Gallic acid 3,5-dimethyl ether, molecular formula $HOC_6H_2(OCH_3)_2CO_2H$.

According to some embodiments, the organic acid component comprises two organic acids selected from the group consisting of anisic acid, levulinic acid; mandelic acid; salicylic acid, sorbic acid, benzoic acid, ferulic acid, and syringic acid, e.g. anisic acid and levulinic acid; anisic acid and mandelic acid; anisic acid and salicylic acid, anisic acid and sorbic acid, anisic acid and benzoic acid, anisic acid and ferulic acid, anisic acid and syringic acid; levulinic acid and mandelic acid, levulinic acid and salicylic acid, levulinic acid and sorbic acid, levulinic acid and benzoic acid, levulinic acid and ferulic acid, levulinic acid and syringic acid; mandelic acid and salicylic acid, mandelic acid and sorbic acid, mandelic acid and benzoic acid, mandelic acid and ferulic acid, mandelic acid and syringic acid; saliculic acid and sorbic acid, salicylic acid and benzoic acid, salicylic acid and ferulic acid, salicylic acid and syringic acid, sorbic acid and benzoic acid, sorbic acid and ferulic acid, sorbic acid and syringic acid; benzoic acid and ferulic acid, benzoic acid and syringic acid; ferulic acid and syringic acid.

According to some embodiments, the organic acids, when used as a combination of two as exemplified above (for example, levulinic acid and anisic acid, etc.), together with glyceryl caprylate/caprate form a broad spectrum preservative effective against microbial contaminants, e.g., bacteria, yeast and mold. Without being limited to any particular theory, the stabilization system comprising glyceryl caprylate/caprate allows for greater penetration of both acids into the cell wall of a targeted organism, which means that the overall concentration of the acids in the formulation is lower, and the concentration of free acid required for full spectrum preservation of the product is reduced. This in turn increases efficacy in challenging finished formulations at a physiological pH, and reduces the need for additional ingredients in the finished formulation without extreme adjustments of the final pH of the finished formulation.

According to some embodiments, the organic acid compound includes any derivative of an organic acid thereof. For example, a derivative of an organic acid that would revert to their acid form when contacted with water, includes, without limitation, an easily hydrolyzable anhydride, mixed anhydride and ester derivatives of the organic acids.

According to some embodiments, the organic acid compound may be employed in any suitable amount. For example, the organic acid compound may be present in the arginine component as about 1.0 wt %, 5.0 wt %, 10.0 wt %, 15.0 wt %, 20.0 wt %, 25.0 wt %, 30.0 wt %, 35.0 wt %, 40.0 wt %, 45.0 wt %, 50.0 wt %, 55.0 wt %, 60.0 wt %, 65.0 wt %, 70.0 wt %, 75.0 wt %, 80.0 wt %, 85.0 wt %, 90.0 wt %, and about 95.0 wt % of the total weight of the arginine component. Exemplary amounts include about 10.0 wt %, to about 70.0 wt % based upon the total weight of the arginine component, about 20 wt % to about 60 wt % based upon the total weight of the arginine component, about 30 wt % to about 50 wt % of the total weight of the arginine component.

According to some such embodiments, the pH is high enough to keep the acid in solution and low enough to keep the glyceryl caprylate/caprate from hydrolyzing. For example, the pH of the raw material cosmetic composition stabilization system in water comprising glyceryl caprylate/caprate can range from pH 4.1-6.9, inclusive, i.e., pH 4.1, 4.2, 4.3, 4.4, 4.5, 4.6, 4.7, 4.8, 4.9, 5.0, 5.1, 5.2, 5.3, 5.43, 5.5, 5.6, 5.7, 5.8, 5.9, 6.0, 6.1, 6.2, 6.3, 6.4, 6.5, 6.6, 6.7, 6.8, 6.9. According to some embodiments, the pH of the finished product/cosmetic composition comprising glyceryl caprylate/caprate ranges from pH 6.0-6.5, inclusive, i.e., pH 6.0, 6.1, 6.2, 6.3, 6.4, or 6.5.

According to some embodiments, the arginine component of the cosmetic composition stabilizing system comprises a solvent. Examples of the solvent may include water, low molecular weight alcohols such as $C_{1-6}$ branched or straight chain alcohols, e.g., methanol, ethanol and isopropanol, low molecular weight ketones such as $C_{1-6}$ branched or straight chain ketones, e.g., acetone, aromatic compounds and low molecular weight alkanes, such as $C_{1-10}$ branched or straight chain alkanes.

According to some embodiments, the arginine component comprises a polar solvent. Exemplary polar solvents include: water; alcohols (such as ethanol, propyl alcohol, isopropyl alcohol, hexanol, benzyl alcohol, polyhydric alcohol); polyols (such as propylene glycol, polypropylene glycol, butylene glycol, hexylene glycol, polyethylene glycols), sugar alcohols (e.g., malitol, sorbitol), glycerine; panthenol dissolved in glycerine, flavor oils and mixtures thereof. Mixtures of these solvents can also be used. According to some embodiments, the solvent is water.

According to some embodiments, the solvent may be employed in any suitable amount. For example, the solvent may be present in the arginine component in about 1.0 wt %, 5.0 wt %, 10.0 wt %, 15.0 wt %, 20.0 wt %, 25.0 wt %, 30.0 wt %, 35.0 wt %, 40.0 wt %, 45.0 wt %, 50.0 wt %, 55.0 wt %, 60.0 wt %, 65.0 wt %, 70.0 wt %, 75.0 wt %, 80.0 wt %, 85.0 wt %, 90.0 wt %, and about 95.0 wt % of the total weight of the arginine component. Exemplary amounts include 10.0 wt %, to about 70.0 wt %, inclusive, based upon the total weight of the arginine component, about 20.0 wt % to about 60.0 wt %, inclusive, based upon the total weight of the arginine component, about 30.0 wt % to about 50.0 wt %, inclusive, of the total weight of the arginine component.

According to some embodiments, the range of pH of the cosmetic or dermatologic formulation stabilizing system, which is within the range of pH 4.1-8.5, inclusive, i.e., pH 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7. 7.8, 7.9, 8.0, 8.1, 8.2, 8.3, 8.4, or 8.5, depends on the organic acids used.

According to some embodiments, the cosmetic composition stabilizing system comprising the arginine component of the present invention may be present as at least about 0.001 wt %, at least 0.005 wt %, at least 0.01 wt %, at least 0.05 wt %, at least 0.10 wt %, at least 0.50 wt %, at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt % of the total weight of the formulation.

According to some embodiments, the cosmetic composition stabilizing system comprising the arginine component of the present invention may be present in about 1.0 wt % to about 100.0 wt %, about 10.0 wt % to 70.0 wt %, or about 20.0 wt % to 50.0 wt % based on the total weight of the formulation. According to some embodiments, the arginine component of the present invention may be present in about 0.001 wt % to 10.0 wt %, about 0.1% to 5.0 wt %, or about 1.0 wt % to 3.0 wt % based on the total weight of the formulation.

Compositions

According to some embodiments, a cosmetic formulation of the present invention may comprise a cosmetically acceptable carrier. According to some embodiments, a dermatologic composition of the present invention may comprise a pharmaceutically acceptable carrier. The carrier may be any suitable excipient, vehicle, component, and/or additive. According to some embodiments, the cosmetic formulations of the present invention comprise one or more cosmetically or pharmaceutically acceptable carrier. According to some embodiments, the cosmetic or dermatologic compositions of the present invention comprise mixtures of two or more carriers.

According to some embodiments, the described finished product/cosmetic composition may comprise antioxidants, chelating agents, conditioners, emulsifiers, emollients, oils, film-forming/polymeric agents, humectants, moisturizing agents, penetration enhancers, pH adjusting agents, powders, preservatives, propellants, surfactants, surface active agents, viscosity enhancing agents, thinning agents, wetting agents, fragrances, colorants, skin care ingredients, active agents, and the like, and any combination thereof.

Antioxidants are agents that minimize or prevent the oxidation process and enhance the shelf life of the composition. Some antioxidants are also useful as skin antioxidants, which minimize the wrinkles and dullness of the skin and provide a more youthful looking and firmer textured skin. Any suitable antioxidant may be used.

According to some embodiments, the antioxidant is derived from a botanical extract. According to some embodiments, antioxidants may be derived from botanical extracts including, green tea extract, black tea extra, white tea extract, *Matricaria recutita* (German chamomile) extract, soy extract, and *Coffea arabica* (coffeeberry)

extract. Exemplary antioxidants may additionally include Vitamin E and its derivatives, including tocopherol, tocopherol acetate, mixed tocopherols (available as COVI-OX T-50 or T-70 from Henkel Corp, Ambler, Pa.), and the like or butylated hydroxytoluene, butylated hydroxyanisole, sodium pyrosulfite, acetone sodium bisulfate and the like.

Chelating agents may increase the stability of the composition of the described invention. Any suitable chelating agent may be used. According to some embodiments, a chelating agent may be derived from a botanical extract. Exemplary chelators that are useful herein are disclosed in U.S. Pat. No. 5,487,884, which is incorporated herein by reference. According to some embodiments, chelating agents may include ethylenediaminetetraacetic acid (EDTA) and its derivatives, thioglycolic acid, thiolactic acid, thioglycerol and the like.

Any suitable conditioner or moisturizer may be used. According to some embodiments, the moisturizer is derived from a botanical extracts. According to some embodiments, the moisturizer may be derived from a botanical extract such as *Matricaria recutita* (German chamomile) extract, soy extract, *Avena sativa* extract, corn oil, cottonseed oil, olive oil, palm kernel oil, rapeseed oil, safflower oil, jojoba oil, evening primrose oil, avocado oil mineral oil, shea butter. According to some embodiments, non-limiting examples of a conditioner may also include alkylamido ammonium lactate, cetrimonium chloride and distearoylethyl hydroxyethylmonium methosulfate and cetearyl alcohol, cetyl dimethicone, cetyl ricinoleate, dimethicone, laureth-23, laureth-4, polydecene, retinyl palmitate, quatemised protein hydrolysates, quatemised cellulose and starch derivatives, quatemised copolymers of acrylic or methacrylic acid or salts, quatemised silicone derivatives.

Any suitable emollient may be used. According to some embodiments, an emollient may be derived from a botanical extract. According to some embodiments, exemplary emollients may include oils, fatty alcohols, fatty acids and esters which aid application and adhesion, yield gloss and provide occlusive moisturization. Other exemplary emollients may include isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl linoleate, pentaerythrityl tetrastearate, neopentylglycol dicaprylate/dicaprate, hydrogenated coco-glycerides, isononyl isononanoate, isotridecyl isononanoate, myristyl myristate, triisocetyl citrate, cetyl alcohol, octyl dodecanol, oleyl alcohol, panthenol, lanolin alcohol, linoleic acid, linolenic acid, sucrose esters of fatty acids, octyl hydroxystearate and mixtures thereof. Examples of other suitable emollients can be found in the Cosmetic Bench Reference, pp. 1.19-1.22 (1996), incorporated herein by reference. Suitable emollients may include polar emollient emulsifiers (such as linear or branched chained polyglycerol esters) and non-polar emollients.

According to some embodiments, a polar emollient is any emollient emulsifier having at least one polar moiety, wherein the solubility (at 30° C.) of a cytoprotective derivative compound in the polar emollient is greater than about 1.5%, greater than about 2%, or greater than about 3%. Exemplary polar emollients may include, but are not limited to, polyol ester and polyol ethers such as linear or branched chained polyglycerol esters and polyglycerol ethers; PG3 diisosterate, polyglyceryl-2-sesquiisostearate, polyglyceryl-5-distearate, polyglyceryl-10-distearate, polyglyceryl-10-diisostearate, acetylated monoglycerides, glycerol esters, glyceryl tricaprylate/caprate, glyceryl ricinoleate, glyceryl isostearate, glyceryl myristate, glyceryl linoleate, polyalkylene glycols such as PEG 600, monoglycerides, 2-monolaurin, sorbitan esters and mixtures thereof.

According to some embodiments, a non-polar emollient is any emollient emulsifier possessing no permanent electric moments (meaning the product of the distance separating the charges of a dipole and the magnitude of either charge). Exemplary non-polar emollients may include, but are not limited to, esters and linear or branched chained hydrocarbons; isononyl isononanoate, isopropyl isostearate, octyl hydroxystearate, diisopropyl dimerate, lanolin oil, octyl palmitate, isopropyl palmitate, pariffins, isoparrifins, acetylated lanolin, sucrose fatty acid esters, isopropyl myristate, isopropyl stearate, mineral oil, silicone oils, dimethicone, allantoin, isohexadecane, isododecane, petrolatum, and mixtures thereof.

The solubility of the organic acid compound in polar or non-polar emollients may be determined according to methods known in the art.

According to some embodiments, the cosmetic compositions may comprise oils that act as emollients also impart viscosity, tackiness, and drag properties to cosmetic compositions such as lipstick. Exemplary oils may include, without limitation, caprylic triglycerides; capric triglyceride; isostearic triglyceride; adipic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hyroxystearate; octyl dodecanol; wheat germ oil; hydrogenated vegetable oils; castor oil; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil mineral oil, shea butter, octylpalmitate, maleated soybean oil, glycerol trioctanoate, diisopropyl dimerate, and volatile and non-volatile silicone oils including phenyl trimethicone.

According to some embodiments, exemplary oils may comprise acetylglycerides, octanoates, and decanoates of alcohols and polyalcohols, such as those of glycol and glycerol, the ricinoleates of alcohols and polyalcohols such as cetyl ricinoleate, PG-3 diisostearate, polyglycerol ethers, polyglyerol esters, caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, castor oil, modified lanolins, octyl palmitate, lanolin oil, maleated soybean oil, cetyl ricinoleate, glyceryl trioctanoate, diisopropyl dimerate, synthetic lanolin derivatives and branched chain alcohols, sucrose esters of fatty acids, octyl hydroxystearate and mixtures thereof.

According to some embodiments, the cosmetic compositions of the described invention may contain an emulsifier/surfactant. Any suitable emulsifier/surfactant may be used. According to some embodiments, the surfactant may be derived from a botanical extract, such as *Hippocastani, Primulae, Hedrae, Ginseng, Quillaja, Glycyrrbizae, Senegae, Polygalae Amarae, Saponariae, Glycine max* and *Herniariae*.

According to some embodiments, the surfactant is nonionic; non-limiting examples include condensation products of long chain alcohols, e.g. $C_{8-30}$ alcohols, with sugar or starch polymers, i.e. glycosides; the condensation products of alkylene oxides with fatty acids (i.e. alkylene oxide esters of fatty acids), which have the general formula $RCO(X)_nOH$ wherein R is a $C_{10-30}$ alkyl group, X is —OCH$_2$CH$_2$— (i.e. derived from ethylene glycol or oxide) or OCH$_2$CHCH$_3$— (i.e. derived from propylene glycol or oxide), and n is an integer from about 6 to about 200; or the condensation products of alkylene oxides with 2 moles of fatty acids (i.e. alkylene oxide diesters of fatty acids), with the general formula $RCO(X)_nOOCR$ wherein R is a $C_{10-30}$ alkyl group, X is —OCH$_2$CH$_2$— (i.e. derived from ethylene glycol or oxide) or —OCH$_2$CHCH$_3$— (i.e. derived from propylene glycol or oxide), and n is an integer from about 6 to about 100.

According to some embodiments, the surfactant is hydrophilic. Non-limiting examples may be seen in McCutcheon's, *Detergents and Emulsifiers*, North American Edition (1986), published by Allured Publishing Corporation; U.S. Pat. No. 5,011,681 to Ciotti et al., issued Apr. 30, 1991; U.S. Pat. No. 4,421,769 to Dixon et al., issued Dec. 20, 1983; and U.S. Pat. No. 3,755,560 to Dickert et al., issued Aug. 28, 1973. According to some embodiments, the surfactant is anionic. Non-limiting examples may be seen in U.S. Pat. No. 3,929,678, to Laughlin et al., issued Dec. 30, 1975, for example, alkoxyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., alkali metal salts, e.g., sodium or potassium salts) of fatty acids.

According to some embodiments, the surfactant may include derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilising group, e.g., carboxy, sulfonate, sulfate, phosphate, or phosphonate. For example, alkyl imino acetates, and iminodialkanoates and aminoalkanoates, imidazolinium and ammonium derivatives; betaines, sultaines, hydroxysultaines, and branched and unbranched alkanoyl sarcosinates, and mixtures thereof.

According to some embodiments, the emulsions include a silicone containing emulsifier or surfactant. Examples of silicone emulsifiers include organically modified organopolysiloxanes, also known to those skilled in the art as silicone surfactants such as dimethicone copolyols. These materials are polydimethyl siloxanes which have been modified to include polyether side chains such as polyethylene oxide chains, polypropylene oxide chains, mixtures of these chains, and polyether chains containing moieties derived from both ethylene oxide and propylene oxide. Other examples include alkyl-modified dimethicone-copolyols, i.e., compounds which contain $C_2$-$C_{30}$ pendant side chains. Still other useful dimethicone copolyols include materials having various charged and uncharged moieties.

According to some embodiments, the cosmetic compositions of the described invention may contain a film-forming polymeric agent. Any suitable film-forming/polymeric agent may be used. The exact surfactant or surfactant mixture chosen will depend upon the pH of the composition and the other components present.

According to some embodiments, the film-forming/polymeric agent may be derived from a botanical extract. According to some embodiments, film-forming/polymeric agents may include polyalkenes, oleophilic copolymers of vinylpyrrolidone, acrylic copolymers, polyethylene glycol derivative, polyolefins, polyurethanes and mixtures thereof.

According to some embodiments, the cosmetic compositions of the described invention may contain a humectant. According to some embodiments, the humectant may be derived from a botanical extract. According to some embodiments, humectants may include esters of polyhydroxy alcohols. Glycolic esters are derived from $C_{2-6}$ glycols, including ethylene glycol, propylene glycol, butylene glycol, hexylene glycol and derivatives thereof, and one or more carboxylic acid moieties having $C_{1-30}$ chains. Exemplary glycolic esters include polyethylene glycols (PEGs), such as PEG-2, PEG-3, PEG-30 and PEG-50, and polypropylene glycols (PPGs), such as PPG-9, PPG-12, PPG-15, PPG-17, PPG-20, PPG-26, PPG-30 and PPG-34.

According to some embodiments, the cosmetic compositions of the described invention may contain a moisturizing agent. Any suitable moisturizing agent may be used. According to some embodiments, the moisturizing agent is derived from a botanical extract. Exemplary moisturizing agents include algae extract, aloe barbadensis, aloe-barbadensis extract, aloe barbadensis gel, althea *officinalis* extract, aluminum starch octenylsuccinate, aluminum stearate, apricot (*Prunus armeniaca*) kernel oil, arginine, arginine aspartate, *Arnica montana* extract, ascorbic acid, ascorbyl palmitate, aspartic acid, avocado (*Persea gratissima*) oil, barium sulfate, barrier sphingolipids, butyl alcohol, beeswax, behenyl alcohol, beta-sitosterol, BHT, birch (*Betula alba*) bark extract, borage (*Borago officinalis*) extract, 2-bromo-2-nitropropane-1,3-diol, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrageenan (*Chondrus crispus*), carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *Eucalyptus globulus* oil, evening primrose (*Oenothera biennis*) oil, fatty acids, fructose, gelatin, geranium *maculatum* oil, glucosamine, glucose glutamate, glutamic acid, glycereth-26, glycerin, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*Corylus americana*) nut oil, hazel (*Corylus avellana*) nut oil, hexylene glycol, honey, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia *ternifolia* nut oil, magnesium stearate, magnesium sulfate, maltitol, matricaria (*Chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (*Citrus aurantium dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, salicylic acid, sandalwood (*Santalum album*) oil, serine, serum protein, sesame (*Sesamum indicum*) oil, shea butter (*Butyrospermum parkii*), silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopherol, tocopheryl acetate, tocopheryl linoleate, tribehenin, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

According to some embodiments, the cosmetic compositions of the described invention may contain a penetration enhancer. Any suitable penetration enhancer may be used. Typically, penetration enhancers will vary depending upon the specific composition embodiment or transdermal formulation, i.e., serum, cream or foam, and the specific penetration enhancer selected.

According to some embodiments, the penetration enhancer may be derived from a botanical extract. According to some embodiments, exemplary penetration enhancers may include, but are not limited to, fatty acids, fatty acid esters, fatty alcohols, fatty acid esters of lactic acid or glycolic acid, glycerol tri-, di- and monoesters, triacetin, short chain alcohols, amine oxides and mixtures thereof. Exemplary permeation enhancers may include oleyl alcohol, lauryl alcohol, isopropyl myristate, oleyl oleate, levulinic acid, ethanol, glycerol monooleate, methyl laurate, sorbitan monooleate, triacetin, aloe vera oil, benzethonium chloride, cetyl dimethylamine oxide, cetyl alcohol, cetyl lactate, cocamidopropyl betaine, cocoamine oxide diethanolamine, dimethyloctylamine oxide, 2-dodecoxyethyldimethylamine oxide, dimethyl-decylamine oxide, dimethylhexadecylamine oxide, dimethyl-tetradecylamine oxide, dimethyl isosorbide, dipropylene glycol, ethyl hexyl lactate, glycolic acid, 3-dodecoxy-2-hydroxypropyldi(3-hydroxypropyl)amine oxide, lactic acid, lauramine oxide, lauryl betaine, lauryl lactate, lauryl laurate, isopropyl palmitate, macrogol 15 hydroxystearate (Solutol HS 15), menthol, menthyl lactate, myristyl alcohol, myristal lactate, octyldodecanol, octyl salicylate, oleamine oxide, oleic acid, oleyl betaine, oleyldi (2-hydroxyethyl) amine oxide, PEG 1000, pentadecalactone, propylene glycol, salicylic acid, stearyl alcohol, stearyl lactate, 3,6,9-trioxaheptadecyl di ethyl amine oxide, di(2-hydroxyethyl)-tetradecylamine oxide, triethanolamine triacetate and combinations thereof. Other exemplary permeation enhancers may be found in U.S. Patent Application Publication No. 2007/0269379, which is incorporated in its entirety herein by reference. Exemplary permeation enhancers include oleyl alcohol, lauryl alcohol, isopropyl myristate, oleyl oleate, levulinic acid, glycerol monooleate, methyl laurate, sorbitan monooleate, triacetin, cetyl alcohol, cetyl lactate, dimethyl isosorbide, dipropylene glycol, ethyl hexyl lactate, glycolic acid, lauramine oxide, lauryl betaine, lauryl lactate, lauryl laurate, isopropyl palmitate, myristyl alcohol, myristal lactate, octyl salicylate, oleamine oxide, oleic acid, oleyl betaine, salicylic acid, stearyl alcohol, stearyl lactate, triethanolamine triacetate and combinations thereof.

According to some embodiments, the cosmetic compositions of the described invention may contain a pH adjusting agent. According to some embodiments, suitable pH adjusting agents will vary depending upon the specific cosmetic composition embodiment or transdermal formulation, location of application, the desired final pH value, and the specific suitable pH adjusting agents selected.

According to some embodiments, the cosmetic compositions of the described invention may contain a powder. According to some embodiments, the powder may be derived from a botanical extract. According to some embodiments, powders may include such as chalk, talc, fullers earth, kaolin, starch, gums, colloidal silica sodium polyacrylate, tetra alkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose, ethylene glycol monostearate, and the like.

According to some embodiments, the cosmetic compositions of the described invention may contain an additional preservative to reduce bacterial growth and odors. According to some embodiments, a preservative may be derived from a botanical extract, such as *Macrocystis pyrifera* extract, *Ascophyllum nodosum* extract, Grapefruit seed extract, *Rosmarinus officinalis* extract, *Chondrus crispus* extract, citric acid, Vitamin E oil, iso-ascobic or erythorbic acid, guar gum, sodium alumninosilicate, honey, *Azadirachta indica* oil, and *Ocimum basilicum* extract.

According to some embodiments, additional exemplary preservatives include propyl paraben, methyl paraben, benzyl alcohol, benzalkonium chloride, tribasic calcium phosphate, phenoxyethanol, or acids such as citric, tartaric, maleic, lactic, malic, benzoic, salicylic and the like.

According to some embodiments, the cosmetic compositions of the described invention may contain a propellant. A propellant dispenses compositions from containers. Any suitable propellant may be used if the composition is an aerosol, foam, or mousse. According to some embodiments, a propellant may be derived from a botanical extract. According to some embodiments, propellants may include nitrogen, carbon dioxide, dimethyl ether, hydrocarbons, i.e., methane, ethane, propane, butanes and pentanes, halogenated hydrocarbons, i.e., $CH_2ClF$, $CClF_2CHClF$, $CF_3CHClF$, $CHF_2CClF_2$, $CHClFCHF_2$, $CF_3CH_2Cl$, $CClF_2CH_3$, $CHF_2CHF_2$, $CF_3CH_2F$ (HFC 134a), $CHF_2CH_3$ (HFC 152a), $CF_3CHFCF_3$ (HFC 227), $CF_3CF_3$ and $CF_3CF_2CF_3$. Some of the more commonly used hydrocarbon propellants are A-46 (15.2% propane/84.8% isobutene); and NP-46 (25.9% propane/74.1% n-butane), NIP-46 (21.9% propane/31.3% isobutene/46.8% n-butane). The amount of propellant will depend on the type of container for the composition of the present invention, the amount of the composition in the container, the amount of composition to be dispensed per actuation and the form in which the composition will be dispensed, i.e., mist or foam. The optimization of the propellant and container are within the ability of the skilled artisan and examples can be found in Wai-Chiu So et al., U.S. Pat. No. 6,946,120 and Remington, Science and Practice of Pharmacy, 21st ed., pp. 1000-1017 which are incorporated in their entirety herein by reference. The propellant is generally not included in the calculation of the weight percentages of the composition prepared in accordance with the present invention because it is merely part of the dispensing device and typically does not remain part of the composition once the composition is dispensed and applied.

According to some embodiments, the cosmetic compositions of the described invention may contain a viscosity enhancing agent or thickener. Viscosity enhancing agents are agents that thicken, gel or harden the composition. According to some embodiments, the viscosity enhancing agent is derived from botanical extracts. Exemplary viscosity enhancing agents include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, *sclerotium* gum, sodium carboyxmethyl dextran, sodium carrageenan, tragacanth gum, xanthan gum, and/or mixtures thereof.

According to some embodiments, viscosity enhancing agents may also include organic materials such as natural or synthetic waxes, $C_{12-60}$ alcohols, $C_{12-60}$ acids, alpha-hydroxy fatty acids, polyhydroxy fatty acid esters, polyhydroxy fatty acid amides, and inorganic/organic materials such as metal ester complexes containing zinc, calcium, aluminum or magnesium, fumed silicas, and organoclays, and mixtures thereof. Additional viscosity enhancing agents include polyol polyesters, glyceryl esters, polyglyceryl esters and polysiloxanes that are a solid or semi-solid at ambient temperature.

According to some embodiments, exemplary viscosity enhancing agents are $C_{12-60}$ alcohols, $C_{16-22}$ fatty alcohols, such as cetyl alcohol, stearyl alcohol, behenyl alcohol and mixtures thereof. Other suitable viscosity enhancing agents include $C_{12-60}$ acids, preferably $C_{12-60}$ fatty acids, such as palmitic acid, stearic acid, behenic acid, oleic acid, linoleic acid, myristic acid, ricinoleic acid, erucic acid, lauric acid, isostearic acid and mixtures thereof. Further exemplary viscosity enhancing agents that may be used herein are alpha-hydroxy fatty acids, including 12-hydroxystearic acid, 12-hydroxylauric acid, 16-hydroxyhexadecanoic acid and mixtures thereof. Additional examples of suitable fatty acids are further described in Klofta et al., U.S. Pat. No. 7,449,613, Hofrichter, et al., U.S. Pat. No. 5,429,816 and Motley, U.S. Pat. No. 5,552,136, disclosure of each is incorporated in its entirety herein by reference.

According to some embodiments, viscosity enhancing agents also include suitable waxes. Natural waxes may include, but are not limited to, carnauba, ozokerite, beeswax, candelilla, paraffin, ceresin, esparto, ouricuri, rezowax and other known mined and mineral waxes. Synthetic waxes may include, but are not limited to, paraffin waxes and microcrystalline waxes.

According to some embodiments, additional exemplary viscosity enhancing agents include polyhydroxy fatty acid esters, polyhydroxy fatty acid amides and mixtures thereof. Esters and amides will have three or more free hydroxy groups on the polyhydroxy moiety and are typically nonionic in character. Because of the possible skin sensitivity of those using articles to which the composition is applied, these esters and amides should also be relatively mild and non-irritating to the skin. Suitable polyhydroxy fatty acid esters and polyhydroxy fatty acid amides are disclosed in Roe et al., U.S. Pat. No. 5,643,588, the disclosure of which is incorporated in its entirety herein by reference.

According to some embodiments, viscosity enhancing agents also include gelling agents, which are materials that can swell or expand when in contact with water. Examples of gelling agents that may be used include swellable polymers, also known as osmopolymers or hydrogels. The swellable polymer can be non-cross-linked or lightly cross-linked. The cross-links can be covalent or ionic bonds with the polymer possessing the ability to swell in the presence of fluid, and when cross-linked it will not be dissolved in the fluid. The polymer can be of plant, animal or synthetic origin. Polymeric materials useful for the present purpose include polyhydroalkylcellulose having a molecular weight greater than 50,000, such as hydroxyl propylmethylcellulose (METHOCEL® K 100M available from Dow Chemical); poly(hydroxyalkylmethacrylate) having a molecular weight of from 5,000 to 5,000,000; poly(vinylpyrrolidone) having a molecular weight of from 100,000 to 3,000,000; anionic and cationic hydrogels; poly(electrolyte) complexes; poly(vinylalcohol) having a low acetate residual; a swellable mixture of agar and carboxymethyl cellulose; a swellable composition comprising methyl cellulose mixed with a sparingly cross-linked agar; a polyether having a molecular weight of from 10,000 to 6,000,000; a water-swellable copolymer produced by a dispersion of a finely divided copolymer of maleic anhydride with styrene, ethylene, propylene, or isobutylene; a water-swellable polymer of N-vinyl lactams and the like.

According to some embodiments, exemplary viscosity enhancing agents also include gelling agents such as pectin having a molecular weight ranging from 30,000 to 300,000; polysaccharides such as agar, acacia, karaya, tragacanth, algins and guar; CARBOPOL®, an acrylic acid polymer, a carboxyvinyl polymer, sometimes referred to as carboxypolymethylene, a polymer of acrylic acid cross-linked with a polyallyl ether of sucrose, as described in U.S. Pat. Nos. 2,798,053 and 2,909,462 and available as CARBOPOL® 934, 940 and 941, and its salt derivatives; polyacrylamides; water-swellable indene maleic anhydride polymers; GOOD-RITE® polyacrylic acid having a molecular weight of 80,000 to 200,000; POLYOX® polyethylene oxide polymers having a molecular weight of 100,000 to 7,000,000; starch graft copolymers; AQUA-KEEP® acrylate polymers with water absorbability of about 400 times its original weight; diesters of polyglucan; a mixture of cross-linked polyvinyl alcohol and poly(N-vinyl-2-pyrrolidone); poly (ethylene glycol) having a molecular weight of 4,000 to 100,000; and mixtures thereof. Representative polymers possessing gelling properties are described in U.S. Pat. Nos. 6,419,954, 4,915,949, 4,327,725, 4,207,893 and in Handbook of Common Polymers, by Scott and Roff, published by Cleveland Rubber Company, Cleveland, Ohio.

According to some embodiments, examples of other inorganic viscosity enhancing agents also include treated and untreated fumed silicas, such as those available from Cabot Corp., Tuscola, Ill. under the trade designations CAB-O-SIL M5 and MS-55, and mixtures thereof. Exemplary surface-treated fumed silicas are also available from Cabot Corp., Tuscola, Ill. under the trade designations TS-720 and TS-610.

According to some embodiments, viscosity enhancing agents also include suitable clays such as hectorite and smectite and mixtures thereof.

According to some embodiments, viscosity enhancing agents also include suitable hydrogenated vegetable oils such as cocoa butter, shea butter and mixtures thereof.

According to some embodiments, the cosmetic composition may optionally comprise one or more skin care ingredients, and/or active agents. According to some embodiments, the skin care ingredient and/or active agent may comprise: anti-acne agents, skin lightening-agents, hair growth agents, hair retardation agents, anti-dandruff agents, anti-irritation agents, anti-oxidants/radical scavenger agents, anti-inflammatory agents, wound-healing agents, anti-viral agents, anti-wrinkle agents, moisturizing agents, anti-fungal, anti-bacterial, enzymes, ceramide, sunscreen, plant extracts, vitamins A/C/D/E, urea, and the like. According to some embodiments, the compositions may comprise two or more skin care ingredients and/or active agents According to some embodiments, the active agent may be derived from a botanical extract such as *Nymphaea gigantea, Syzygium moorei, Cupaniopsis anacardioides, Archidendron hendersonii, Tristaniopsis laurina Brachychiton acerifolius, Stenocarpus sinuatus, Alphitonia excelsa, Eucalyptus coolabah, Plumeria alba, Cocos nucifera, Tamarindus indica*, and the like. According to some embodiments, the active agent may be derived from a botanical extract such as an essential oil, for example sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, *eucalyptus* oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and/or ylang ylang oil.

Methods

According to some embodiments, the described invention provides a method for preparing a cosmetic composition stabilizing system comprising an effective amount of an arginine component. According to some embodiments, the arginine component comprises i) arginine, or a conjugate, or an analog thereof, ii) an organic acid, its conjugate, or derivative thereof, and iii) a solvent. As used herein, the phrase "arginine, its conjugate, or an analog thereof" is referred to as an "arginine compound." As used herein, the phrase "organic acid, its conjugate, or a derivative thereof" is referred to as an "organic acid compound." According to some embodiments the arginine component comprises i) an arginine compound, ii) an organic acid compound, and iii) a solvent. Without being limited to any particular theory, according to some embodiments, the arginine compound neutralizes the organic acid compound.

According to some embodiments, the cosmetic composition stabilizing system comprises a wetting agent. The glyceryl monoesters (e.g., (Glyceryl Laurate, Glyceryl Laurate SE, Glyceryl Laurate/Oleate, Glyceryl Adipate, Glyceryl Alginate, Glyceryl Arachidate, Glyceryl Behenate, Glyceryl Caprate, Glyceryl Caprylate, Glyceryl Caprylate/Caprate, Glyceryl Citrate/Lactate/Linoleate/Oleate, Glyceryl Cocoate, Glyceryl Collagenate, Glyceryl Erucate, Glyceryl Hydrogenated Rosinate, Glyceryl Hydrogenated Soyate, Glyceryl Hydroxystearate, Glyceryl Isopalmitate, Glyceryl Isostearate, Glyceryl Isostearate/Myristate, Glyceryl Isostearates, Glyceryl Lanolate, Glyceryl Linoleate, Glyceryl Linolenate, Glyceryl Montanate, Glyceryl Myristate, Glyceryl Isotridecanoate/Stearate/Adipate, Glyceryl Oleate SE, Glyceryl Oleate/Elaidate, Glyceryl Palmitate, Glyceryl Palmitate/Stearate, Glyceryl Palmitoleate, Gyceryl Pentadecanoate, Glyceryl Polyacrylate, Glyceryl Rosinate, Glyceryl Sesquioleate, Glyceryl/Sorbitol Oleate/Hydroxystearate, Glyceryl Stearate/Acetate, Glyceryl Stearate/Maleate, Glyceryl Tallowate, Glyceryl Thiopropionate, Glyceryl Undecylenate), occur primarily as white to yellow oils or oily waxes. Glyceryl Caprylate/Caprate is a mixture of monoesters, Glyceryl Caprylate and Glyceryl Caprate. According to some embodiments, the wetting agent is glyceryl caprylate/caprate. According to some embodiments, the glyceryl caprylate/caprate is added in solution at the end of production under ambient temperature when the formula structure has formed and not as a raw material. Without being limited by theory, according to some embodiments, the glyceryl caprylate/caprate enhances the surface active properties of the cosmetic composition.

According to some embodiments, the pH of the finished product ranges from about pH 4.5 to about 5.5, inclusive, i.e., 4.5, 4.6, 4.7, 4.8, 4.9, 5.0, 5.1, 5.2, 5.3, 5.4, 5.5. According to some embodiments, the pH of the finished product may be between pH 4.5 and 6.5, inclusive, i.e., pH 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, or 6.9.

According to some embodiments, the pH of the finished product/cosmetic composition ranges from pH 4.5 to pH 5.5 inclusive, i.e., 4.5, 4.6, 4.7, 4.8, 4.9, 5.0, 5.1, 5.2, 5.3, 5.4, 5.5 . . . . According to some embodiments, the pH of the finished product ranges from pH 4.5 and 6.5, inclusive, i.e., pH 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5. According to some embodiments, where the stabilizing system comprises glyceryl caprylate/caprate, the pH of the finished product/cosmetic composition stabilizing system ranges from pH 6.0-6.5, inclusive, i.e., pH 6.0, 6.1, 6.2, 6.3, 6.5.

According to some embodiments, the described invention also provides methods for preparing stable cosmetic or dermatologic compositions comprising combining a cosmetic composition stabilizing system comprising an arginine component comprising i) an arginine compound, ii) an organic acid compound, and iii) a solvent; with one or more cosmetically or pharmaceutically acceptable carriers; and one or more active agents.

According to some embodiments, the arginine component is prepared by reacting the arginine compound with the organic acid compound in the solvent. According to some embodiments, the arginine component is prepared by dissolving or suspending the arginine compound in the solvent and reacting the solution with the organic acid.

According to some embodiments, the arginine component is prepared by forming an arginine-organic acid complex in the solvent. According to some embodiments, the arginine-organic acid complex is formed by reacting the arginine compound with the organic acid compound in the solvent. According to some embodiments, the arginine-organic acid complex is prepared by dissolving or suspending the arginine compound in the solvent and reacting the solution with the organic acid.

According to some embodiments, the arginine-organic acid complex is formed through non-bonded interactions. According to some embodiments, the non-bonded interactions comprise hydrogen bonds. According to some embodiments, the non-bonded interactions comprise salt bridges.

According to some embodiments, the described invention provides methods for manufacturing stable cosmetic or dermatologic compositions comprising the cosmetic stabilizing system comprising the arginine component as an ingredient in a cosmetic or dermatologic composition.

According to some embodiments, provided herein are methods of efficient manufacture for stable cosmetic or dermatologic compositions comprising preparing the cosmetic composition stabilizing system comprising the arginine component as described herein, and using the arginine component as an ingredient in a cosmetic or dermatologic composition in place of one or more, two or more, three or more, four or more, and the like, ingredients in a cosmetic product.

According to some embodiments, provided herein are methods of efficient manufacture for stable cosmetic or dermatologic compositions comprising preparing cosmetic composition stabilizing system comprising the arginine component as described herein, and using the arginine component as a multifunctional ingredient.

Uses

According to some embodiments, the described invention comprising greater than 20% (w/w %) organic acids, is effective to achieve higher solution concentrations of solid (crystal form, insoluble only) organic acids without crystallization and without any additional solvent, glycol, glycerol or the like to inhibit crystallization over long periods of time, including freezing and refrigeration.

According to some embodiments, where a particular formula shows difficulty in controlling microbial growth, organic acid effectiveness is enhanced with the addition of a wetting agent, such as glyceryl caprylate/caprate (glyceryl monoester and acrylic fatty acid). According to some such embodiments, the wetting agent, especially in combination with organic acids, has a boosting effect against bacteria and yeast. According to some embodiments, the wetting agent destabilizes the cell membranes of the microorganisms allowing the organic acids to penetrate more easily into the cells where they disturb the cell's metabolism, leading to cell death.

Wetting agents like glyceryl caprylate/caprate are pH restrictive in that hydrolysis begins to occur at a pH of over 7 and at a pH under a pH of 4 as well as at higher temperatures destabilizing cosmetic emulsions and rendering them ineffective. In contrast, for effectiveness in cosmetic preparations, organic acids and their solutions require higher pH (generally greater than 7) to be incorporated into a useable solution. This proves challenging in achieving the benefits of both in one solution, as the raising and lowering of pH in one system can negatively impact the formula. In addition, wetting agents in this category tend to be waxy and not 100% soluble and can cloud formulas or not incorporate fully requiring additional surfactants or long mixing time at elevated temperature.

Separately, organic acids in normally neutralized solutions almost always require a pH range >7 and more often than not above 8. The general rule is that the higher the concentration of acid the higher the pH requirement but there are limits under this rule.

Systems with wide swings in pH and requirements for pH adjusting ingredients like sodium or ammonium hydroxide to raise pH, or in contrast lactic or citric acids to lower pH can and will destabilize emulsions, affect other ingredients and require particular attention to long term stability. The described invention erases that step almost entirely with the described cosmetic composition stabilization system. As delivered this stabilization system is in the pH range of most cosmetic formulas (4.0-7.0) and if any final adjustment of a formula is required, it is generally low. The stabilization system therefore reduces the chance for instability with free salts or acids.

The described invention achieves (at a pH<7) a fully broad-spectrum cosmetic composition stabilizing system using two organic acids selected from anisic acid, levulinic acid, mandelic acid, salicylic acid, sorbic acid, benzoic acid, ferulic acid, and syringic acid, and the other organic acids exemplified above and a wetting agent, namely glyceryl caprylate/caprate. The combination of the organic acids and the wetting agent produces a synergistic result despite their seemingly incompatibility, since the acid requires high temperature, high neutralizing pH, and the wetting agent requires low temperature and lower pH. The described invention reduced the pH requirement to pH<7 to achieve solutions of organic acids at a >20% (w/w %) concentration without including a humectant, and a clear stable solution resulted where the solubility of the wetting agent was enhanced to achieve clarity and remained clear over multiple freeze thaw cycles.

The described invention provides an enhanced antimicrobial effect, ease of use by addition to formulation at room temperature, and a 100% clear, fully soluble stabilizing system, which can be added at any phase of cosmetic formulation at ambient temperature or temperature <80° C. in one system. Another benefit of the described cosmetic composition stabilizing system is that this is achieved at use levels relatively low in comparison to other complexes that offer broad spectrum activity. The addition of the wetting agent allows for greater efficacy at higher pH than using the organic acid alone. Using the organic acid alone, requires a H range from pH 4.5-5.5; but efficacy is achieved even at pH of 6 with the addition of glyceryl caprylate/caprate.

According to some embodiments, the described stabilization system formulations are effective to preserve cosmetic and dermatologic products without addition of a chemical preservative. According to some embodiments, the preservation of cosmetic and dermatologic products may be characterized as reducing decomposition due to chemical change or the action of microbes, bacteria, fungi, and/or yeast in a cosmetic product.

According to some embodiments, the described stabilization system formulations are useful for stabilizing cosmetic and dermatologic products. The stabilization of cosmetic and dermatologic product may be characterized as reducing decomposition due to chemical change or microbial action in a cosmetic product.

According to some embodiments, the described stable cosmetic formulations are useful for treating skin. The treatment of skin may be characterized as improving the appearance of skin. "Improving the appearance of skin" includes one or more of the following: improving the appearance of skin health, thickness, texture, smoothness, tone, and hydration. The term "improving the appearance of skin" further includes one or more of the following: reducing the appearance of skin inflammation, uneven pigmentation, damage, scars, abrasions, dryness, pore size, fine lines and wrinkles. The method for treating the skin of a subject comprises the step of administering a composition containing an effective amount of the arginine component described herein.

According to some embodiments, the described cosmetic stabilization system formulations are useful for improving the efficiency of the manufacture of stable cosmetic or dermatologic compositions.

All referenced journal articles, patents, and other publications are incorporated by reference herein in their entirety.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1. Exemplary Formulation I (pH 5-5.5)

| INCI Name | Wt % |
| --- | --- |
| Water | 40.00 |
| Arginine | 32.73 |
| Levulinic Acid | 18.18 |
| Benzoic Acid | 9.09 |
| Total | 100.0 |

Example 2. Exemplary Formulation 2 (pH 8-8.5)

| INCI Name | Wt % |
| --- | --- |
| Water | 16.50 |
| Arginine | 7.20 |
| p-Anisic Acid | 6.30 |
| Phenoxyethanol | 70.00 |
| Total | 100.0 |

Example 3. Exemplary Formulation 3 (pH 8-8.5)

| INCI Name | Wt % |
| --- | --- |
| Water | 40.20 |
| Arginine | 35.80 |
| Levulinic Acid | 16.00 |
| p-Anisic Acid | 8.00 |
| Total | 100.0 |

Example 4. Exemplary Formulation 4 (pH 4.6)

| INCI Name | Wt % |
| --- | --- |
| Arginine | 20.00 |
| Levulinic Acid | 50.00 |
| Water | 30.00 |
| Total | 100.0 |

Example 5. Exemplary Formulation 5 (pH 7-8.0)

| INCI Name | Weight % |
| --- | --- |
| Arginine | 36.00 |
| Water | 34.00 |
| p-Anisic Acid | 31.00 |
| Total | 100.0 |

Example 6. Exemplary Formulation 6 (pH 7.5-8.5)

| INCI Name | Wt % |
| --- | --- |
| Arginine | 25.00 |
| Water | 54.00 |
| Mandelic Acid | 21.00 |
| Total | 100.0 |

Example 7. Exemplary Formulation 7 (pH 6.0-6.5)

| INCI Name | Wt % |
| --- | --- |
| Water | 67.50 |
| Arginine anisate | 7.50 |
| Arginine levulinate | 15.00 |
| Glyceryl caprylate | 10.00 |
| Total | 100.0 |

Example 8. Exemplary Formulation 8 (pH 6.5-6.90)

| INCI Name | Wt % |
| --- | --- |
| Water | 67.0 |
| Arginine levulinate | 15.0 |
| Arginine benzoate | 5.50 |
| Glyceryl caprylate | 12.5 |
| Total | 100.0 |

Example 9. Exemplary formulation 9 (pH 6.5-6.9)

| INCI Name | Wt % |
| --- | --- |
| Water | 69.00 |
| Arginine benzoate | 9.00 |
| Arginine salicylate | 12.00 |
| Glyceryl caprylate | 10.00 |
| Total | 100.0 |

Example 10. Exemplary formulation 10 (pH 6.0-6.5)

| INCI Name | Wt % |
| --- | --- |
| Water | 67.00 |
| Arginine mandelate | 13.00 |
| Arginine Benzoate | 8.00 |
| Glyceryl caprylate | 12.00 |
| Total | 100.0 |

Example 11. In Vivo Evaluation of the Improvement of Skin

In vivo evaluation of the compositions of the described invention will be performed in human volunteers following the administration of exemplary compositions topically. Improvement of one or more parameters of the appearance of skin, e.g., thickness, texture, smoothness, tone, hydration; reducing the appearance of skin inflammation, uneven pigmentation, damage, scars, abrasions, dryness, pore size, fine lines and wrinkles, will be evaluated.

For example, the volunteers may be divided into a group for each test formulations Formulations 1-10, and a control group. The topical compositions comprising the cosmetic composition stabilization system may be administered directly or mixed with one or more active agents and/or cosmetically or pharmaceutically acceptable carriers and applied to the arm skin of each volunteer. Each test formulation may be administered to the respective test group twice daily for up to 90 days.

Evaluations in the improvements in the appearance of skin may be based on the appearance of the skin of the respective test groups as compared to the appearance of the skin of the control group. Improvements in the appearance of skin may persist as long as administration continues.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

The invention claimed is:

1. A cosmetic or dermatologic composition raw material containing an arginine-component comprising
   i) a complex consisting essentially of an arginine compound and one carboxylic acid selected from anisic acid, levulinic acid, mandelic acid, sorbic acid, benzoic acid, ferulic acid, and syringic acid or two carboxylic acids selected from anisic acid, levulinic acid, mandelic acid, salicylic acid, sorbic acid, benzoic acid, ferulic acid, and syringic acid, wherein said complex does not comprise a humectant, and
   ii) a solvent;
   wherein the arginine compound is an arginine, a conjugate, or an analog thereof represented by Formula VI,

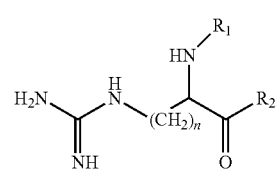

Formula VI wherein
$R_1$ represents
a hydrogen atom, a hydroxyl group, an acyl or acyloxy radical, or an amino acid substituted or not on its free a-amino function, bound by a peptide bond;

R₂ represents
  a hydroxyl group, an amine, alkylamine or alcoxy radical, a silyloxy group, or an amino acid substituted or not on its free α-carboxylic function, bound by a peptide bond;
n represents 3 or 4;
wherein properties of the raw material include:
solubilization of each of the one or two carboxylic acids by the complex;
a humectant with water-attracting properties is unnecessary to stabilize the organic acids in solution, wherein the humectant is a glycerol, a glycol, an ester of polyglycerol, a glycolic ester, and/or an ester of sorbitan;
pH of the raw material ranges from 4.0 to 7.0, inclusive;
the raw material remains clear over multiple freeze thaw cycles;
preservation of a finished cosmetic and dermatologic product by reduction of its decomposition due to chemical change or action of microbes, bacteria, fungi, yeast or a combination thereof without addition of a chemical preservative; and
stabilization of the finished cosmetic and dermatologic product at pH 4.5-5.5. inclusive.

2. The cosmetic or dermatologic composition raw material according to claim 1, wherein the solvent is water.

3. A method of preparing the cosmetic or dermatologic composition comprising the raw material according to claim 1 comprising
  a. preparing each of the one or two carboxylic acids of the cosmetic or dermatologic composition preservative as a greater than 20% solution (w/w %) to form the carboxylic acid compound;
  b. combining the arginine compound and each of the carboxylic acid compounds to form a cosmetic or dermatologic composition complex consisting essentially of an arginine compound and one carboxylic acid selected from anisic acid, levulinic acid, mandelic acid, sorbic acid, benzoic acid, ferulic acid, and syringic acid or two carboxylic acids selected from anisic acid, levulinic acid, mandelic acid, salicylic acid, sorbic acid, benzoic acid, ferulic acid, and syringic acid, wherein said complex does not comprise a humectant;
  c. combining the cosmetic composition complex and a cosmetically or pharmaceutically acceptable carrier, to form the cosmetic or dermatologic composition raw material; and
  d. adjusting pH of the cosmetic or dermatologic composition as needed to 4.5-5.5, inclusive;
wherein decomposition of the cosmetic or dermatologic composition due to chemical change or the action of microbes, bacteria, fungi, yeast or a combination thereof is reduced without addition of a chemical preservative and the cosmetic or dermatologic composition is stabilized at pH 4.5-5.5, inclusive.

4. The method of preparing the cosmetic or dermatologic composition raw material according to claim 3, further comprising formulating the cosmetic or dermatologic composition with an active agent for topical application.

5. A method of treating a skin condition of a subject in need thereof comprising preparing the cosmetic or dermatologic composition comprising the raw material and the active agent according to claim 4, and administering the cosmetic or dermatologic composition comprising the active agent topically to the subject, wherein the active agent comprises one or more of an anti-acne agent, a skin lightening-agent, a hair growth agent, a hair retardation agent, an anti-dandruff agent, an anti-irritation agent, an anti-oxidants/radical scavenger agent, an anti-inflammatory agent, a wound-healing agent, an anti-viral agent, an anti-wrinkle agent, a moisturizing agent, an anti-fungal agent, an anti-bacterial agent, an enzyme, a ceramide, a sunscreen, a plant extract, a vitamin, or urea.

6. A cosmetic or dermatologic composition raw material comprising an arginine-component and a glyceryl monoester wetting agent, wherein, the arginine component comprises
  i) a complex consisting essentially of an arginine compound and two carboxylic acids selected from anisic acid, levulinic acid, mandelic acid, salicylic acid, sorbic acid, benzoic acid, ferulic acid, and syringic acid, wherein said complex does not comprise a humectant, and ii) a solvent;
wherein the arginine compound is an arginine, a conjugate, or an analog thereof represented by Formula VI,

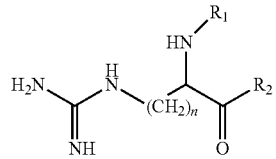

Formula VI wherein
R₁ represents
  a hydrogen atom, a hydroxyl group, an acyl or acyloxy radical, or an amino acid substituted or not on its free a-amino function, bound by a peptide bond;
R₂ represents
  a hydroxyl group, an amine, alkylamine or alcoxy radical, a silyloxy group, or an amino acid substituted or not on its free a-carboxylic function, bound by a peptide bond;
n represents 3 or 4;
wherein properties of the raw material include:
solubilization of each of the one or two carboxylic acids by the complex;
a humectant with water-attracting properties is unnecessary to stabilize the organic acids in solution, wherein the humectant is a glycerol, a glycol, an ester of polyglycerol, a glycolic ester, and/or an ester of sorbitan;
pH of the raw material ranges from 4.0 to 7.0, inclusive;
the raw material remains clear over multiple freeze thaw cycles;
preservation of a finished cosmetic and dermatologic product by reduction of its decomposition due to chemical change or the action of microbes, bacteria, fungi, yeast or a combination thereof without addition of a chemical preservative; and
stabilization of the finished product by the raw material at pH 6.0-6.5, inclusive.

7. The cosmetic or dermatologic composition raw material according to claim 6, wherein the glyceryl monoester wetting agent is glyceryl caprylate/caprate.

8. The cosmetic or dermatologic composition raw material according to claim 6, wherein the solvent is water.

* * * * *